(12) United States Patent
Sharma et al.

(10) Patent No.: US 7,054,818 B2
(45) Date of Patent: May 30, 2006

(54) MULTI-MODAL INFORMATION RETRIEVAL SYSTEM

(75) Inventors: Dipanshu Sharma, San Diego, CA (US); Sunil Kumar, San Diego, CA (US); Chandra Kholia, San Diego, CA (US)

(73) Assignee: V-Enablo, Inc., La Jolla, CA (US)

( * ) Notice: Subject to any disclaimer, the term of this patent is extended or adjusted under 35 U.S.C. 154(b) by 149 days.

(21) Appl. No.: 10/761,650

(22) Filed: Jan. 14, 2004

(65) Prior Publication Data

US 2004/0172254 A1 Sep. 2, 2004

Related U.S. Application Data

(60) Provisional application No. 60/439,981, filed on Jan. 14, 2003.

(51) Int. Cl.
*G10L 21/00* (2006.01)
(52) U.S. Cl. .................... 704/270; 704/270.1
(58) Field of Classification Search ........ 704/270–275; 707/9; 712/1
See application file for complete search history.

(56) References Cited

U.S. PATENT DOCUMENTS

| | | | | |
|---|---|---|---|---|
| 6,088,675 A | * | 7/2000 | MacKenty et al. | 704/270 |
| 6,115,686 A | * | 9/2000 | Chung et al. | 704/270 |
| 6,418,439 B1 | * | 7/2002 | Papierniak et al. | 707/9 |
| 2002/0178344 A1 | * | 11/2002 | Bourguet et al. | 712/1 |
| 2002/0198719 A1 | * | 12/2002 | Gergic et al. | 704/270.1 |

* cited by examiner

*Primary Examiner*—David D. Knepper
(74) *Attorney, Agent, or Firm*—Fish & Richardson P.C.

(57) ABSTRACT

Multi-modal system which enables documents to be interpreted as either or both of voice browser-based documents and/or visual browser-based documents for a thin client such as a portable telephone. Special techniques and additions are added into the document to enable the document to be converted between voice markup and visual markup languages. In addition, the document can be simultaneously viewed in both of the voice markup and the visual markup languages. Special techniques are used to allow keeping track of the browsing position within this document.

45 Claims, 15 Drawing Sheets

MULTI-MODAL INFORMATION RETRIEVAL SYSTEM

CROSS-REFERENCE TO RELATED APPLICATIONS

This application claims priority under 35 U.S.C. 119(e)(1) to (i) U.S. Provisional Patent Application No. 60/439,981, filed Jan. 14, 2003, which is related to U.S. patent application Ser. No. 10/040,525, entitled INFORMATION RETRIEVAL SYSTEM INCLUDING VOICE BROWSWER AND DATA CONVERSION SERVER, (ii) United States Provisional Application No. 60/348,579, entitled DATA CONVERSION SERVER FOR VOICE BROWSING SYSTEM, and (iii) United States Provisional Application No. 60/350,923, entitled MULTI-MODE PLATFORM FOR INFORMATION RETRIEVAL SYSTEM.

COMPUTER PROGRAM LISTING APPENDIX

A CD-ROM containing computer program listings identified as Appendices A–D has been filed in connection herewith (having a file entitled 10469052.doc thereon), the contents of which are hereby fully incorporated by reference.

FIELD

The present invention relates to the field of browsers used for accessing data in distributed computing environments, and, in particular, to techniques for accessing such data in a multi-modal manner using Web browsers controlled at least in part through voice commands.

BACKGROUND

The World Wide Web, or simply "the Web", is comprised of a large and continuously growing number of Web pages which are accessible over a publically-available network. Clients request information, e.g., Web pages, from Web servers; using the Hypertext Transfer Protocol ("HTTP"). HTTP is a protocol which provides users access to files including text, graphics, images, and sound using a mark-up language that forms a page description language known as the Hypertext Markup Language ("HTML"). HTML provides document formatting allowing the developer to specify the look of the document and/or links to other servers in the network. A Uniform Resource Locator (URL) defines the path to Web site hosted by a particular Web server.

The pages of Web sites are typically accessed using an HTML-compatible browser (e.g., Netscape Navigator or Internet Explorer) executing on a client machine. The browser specifies a link to a Web server and particular Web page using a URL. When the user of the browser specifies a link via a URL, the client issues a request to a domain name server (DNS) to map a hostname in the URL to a particular network IP address at which the server is located. The DNS returns a list of one or more IP addresses that can respond to the request. Using one of the IP addresses, the browser establishes a connection to a Web server. If the Web server is available, it returns a document or other object from the web server formatted according to HTML.

As Web browsers become the primary interface for access to many network and server services, Web applications in the future will need to interact with many different types of client machines including, for example, conventional personal computers and recently developed "thin" clients. Thin clients can range between 60 inch TV screens to handheld mobile devices. This large range of devices creates a need to customize the display of Web page information based upon the characteristics of the graphical user interface ("GUI") of the client device requesting such information. Conventional technology often uses HTML pages or scripts that are customized to handle the GUI and navigation requirements of each of these clients.

Client devices having different display capabilities, which may be monochrome, color, different color palettes, resolution, sizes. Such devices may also have multiple peripheral devices that may be used to provide input signals or commands (e.g., mouse and keyboard, touch sensor, remote control for a TV set-top box). Furthermore, the browsers executing on such client devices can support different languages (e.g., HTML, dynamic HTML, XML, Java, JavaScript). These differences may cause the experience of browsing the same Web page to differ dramatically, depending on the type of client device employed.

The inability to adjust the display of Web pages based upon a client's capabilities and environment may cause certain drawbacks. For example, a Web site may simply be incapable of servicing a particular set of clients, or may make the Web browsing experience confusing or unsatisfactory in some way. Even if the developers of a Web site have made an effort to accommodate a range of client devices, the code for the Web site may need to be duplicated for each client environment. Duplicated code consequently increases the maintenance cost for the Web site. In addition, entirely different URLs may be needed to access the Web pages formatted for specific types of client devices.

Content from Web pages has been generally been inaccessible to those users not having a personal computer or other hardware device similarly capable of displaying Web content. Even if a user possesses such a personal computer or other device, the user needs to have access to a connection to the Internet. In addition, those users having poor vision or reading skills are likely to experience difficulties in reading text-based Web pages.

For these reasons, efforts have been made to develop Web browsers for facilitating non-visual access to Web pages for users that wish to access Web-based information or services through a telephone. Such non-visual Web browsers, or "voice browsers", or "speech browsers", present audio output to a user by converting the text of Web pages to speech and by playing pre-recorded Web audio files from the Web. A voice browser also permits a user to navigate between Web pages by following hypertext links, as well as to choose from a number of pre-defined links, or "bookmarks" to selected Web pages. In addition, certain voice browsers permit users to pause and resume the audio output by the browser.

The Voice eXtensible Markup Language ("VoiceXML") is a markup language developed specifically for voice applications useable over the Web, and is described at http://www.voicexml.org. VoiceXML defines an audio interface through which users may interact with Web content, similar to the manner in which the Hypertext Markup Language ("HTML") specifies the visual presentation of such content. In this regard, VoiceXML includes intrinsic constructs for tasks such as dialogue flow, grammars, call transfers, and embedding audio files.

Unfortunately, the VoiceXML standard generally contemplates that VoiceXML-compliant voice browsers interact exclusively with Web content that is in a special VoiceXML format. This has limited the utility of existing VoiceXML-compliant voice browsers, since a relatively small percentage of Web sites include content that is formatted in accordance with VoiceXML.

In addition to the large number of HTML-based Web sites, Web sites serving content conforming to standards applicable to particular types of user devices are becoming increasingly prevalent. For example, the Wireless Markup Language ("WML") of the Wireless Application Protocol ("WAP") (see, e.g., http://www.wapforum.org/) provides a standard for developing content applicable to wireless devices such as mobile telephones, pagers, and personal digital assistants. Some other standards for Web content include the Handheld Device Markup Language ("HDML"), and the relatively new Japanese standard Compact HTML.

BRIEF DESCRIPTION OF THE DRAWINGS

Reference should be made to the following detailed description taken in conjunction with the accompanying drawings, in which.

DETAILED DESCRIPTION

In order to understand the concepts described herein, a detailed explanation of how information is transferred in multi-modal form is first provided. The following description describes how web based documents in some mark-up language form can be obtained and converted between different forms including speech browsing, here described in terms of VoiceXML, and visual browsing, here described in terms of WAP browsing. It should be understood that any speech mark-up language can be used in place of VoiceXML; although VoiceXML is described as the preferred technique used herein. Similarly, while compact visualXML languages such as xHTML are described as being used for the WAP browsing, it should be understood that other similar languages can be used.

Also, the term "display", "play", and "browsing" are used to refer to both display of visual information and the playing of speech information.

According to the techniques described herein, a special document can be provided which is capable of being displayed in either or both of VoiceXML and compact HTML. This can allow a user, for example, both to view a web page in xHTML on a telephone, and at the same time to play the audio in speech XML. Techniques are also described for allowing the user to switch back-and-forth between VoiceXML and contact visual XML.

INTRODUCTORY OVERVIEW

The present disclosure provides a system and method for transferring information in multi-modal form; that is simultaneously in both visual and voice form; in accord with user preference. A technique is disclosed which enables existing visual and voice-based content to be combined and delivered to users in multi-modal form. In an exemplary embodiment, the user is provided with the opportunity to select the mode of information presentation and to switch between modes.

As is described herein, a user is permitted to interact with different portions of existing content using either a visual or voice-based communication modes. The decision as to whether to "see" or "listen" to content will generally depend upon either or both of the type of the content being transferred and the context in which the user is communicating intelligent switching of modes from voice to visual, and vice-versa, in accordance with the differing types of various portions of existing content is also described. The basic description of the Multi-modal operation begins with FIG. 8, herein.

Exemplary Single-Mode Information Retrieval System

Figure 1:
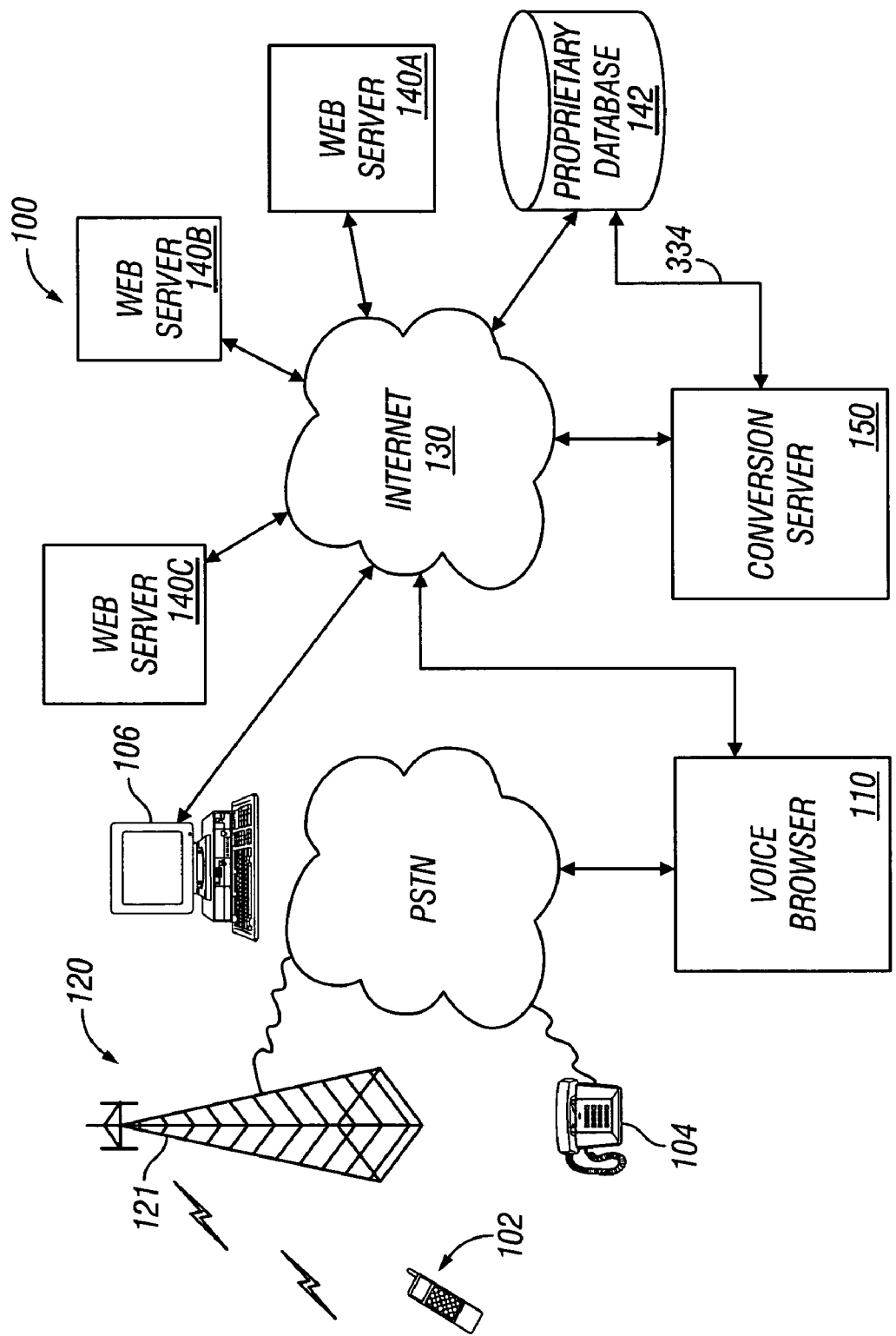
FIG. 1 provides a schematic diagram of a system for accessing Web content using a voice browser system in accordance with the present invention.

FIG. 1 provides a schematic diagram of a system 100 for accessing Web content using a voice browser in a primarily single-mode fashion. The system 100 includes a telephonic subscriber unit 102 in communication with a voice browser 110 through a telecommunications network 120. The voice browser 110 communicates with a user of the subscriber unit 102 on the basis of document files comporting with a known speech mark-up language (e.g., VoiceXML). The voice browser 110 initiates, in response to requests for content submitted through the subscriber unit 102, the retrieval of information forming the basis of certain such document files from remote information sources. Such remote information sources may comprise, for example, Web servers 140a, 140b, 140c and one or more databases represented by proprietary database 142.

The voice browser 110 initiates such retrieval by issuing a browsing request either directly to the applicable remote information source or to a conversion server 150. If the request for content pertains to a remote information source operative in accordance with the protocol applicable to the voice browser 110, here VoiceXML), then the voice browser 110 issues a browsing request directly to the remote information source of interest. For example, when the request for content pertains to a Web site supporting VoiceXML, a document file containing such content is requested by the voice browser 110 via the Internet 130 directly from the Web server 140a hosting the Web site of interest.

When a request for content issued through the subscriber unit 102 identifies a Web site that does not support VoiceXML, the voice browser 110 issues a corresponding browsing request to a conversion server 150. The conversion server 150 retrieves content from the Web server 140b hosting the Web site of interest and converts this content into a document file compliant with VoiceXML. The converted document file is then provided by the conversion server 150 to the voice browser 110, which then uses this file to effect a dialogue conforming to VoiceXML with the user of subscriber unit 102.

Similarly, when a request for content identifies a proprietary database 142, the voice browser 110 issues a corresponding browsing request to the conversion server 150. In response, the conversion server 150 retrieves content from the proprietary database 142 and converts this content into a document file compliant with VoiceXML. The converted document file is then provided to the voice browser 110 and used as the basis for carrying out a dialogue with the user of subscriber unit 102.

As shown in FIG. 1, the subscriber unit 102 is in communication with the voice browser 110 via the telecommunications network 120. The subscriber unit 102 has a keypad (not shown) and associated circuitry for generating Dual Tone MultiFrequency (DTMF) tones. The subscriber unit 102 transmits DTMF tones to, and receives audio output from, the voice browser 110 via the telecommunications network 120. The subscriber unit 102 may communicate via a mobile station 121 and the telecommunications network 120 is represented as including a mobile communications network and the Public Switched Telephone Network ("PSTN") 122. However, the voice-based information retrieval services offered by the system 100 can be accessed by subscribers through any type of telecommunication parts. For example, the voice browser 110 may be accessed through the PSTN from, for example, a stand-alone telephone 104 (either analog or digital), or from a node on a PBX. In addition, a personal computer 106 or other handheld or portable computing device disposed for voice over IP communication may access the voice browser 110 via the Internet 130.

Figure 2:
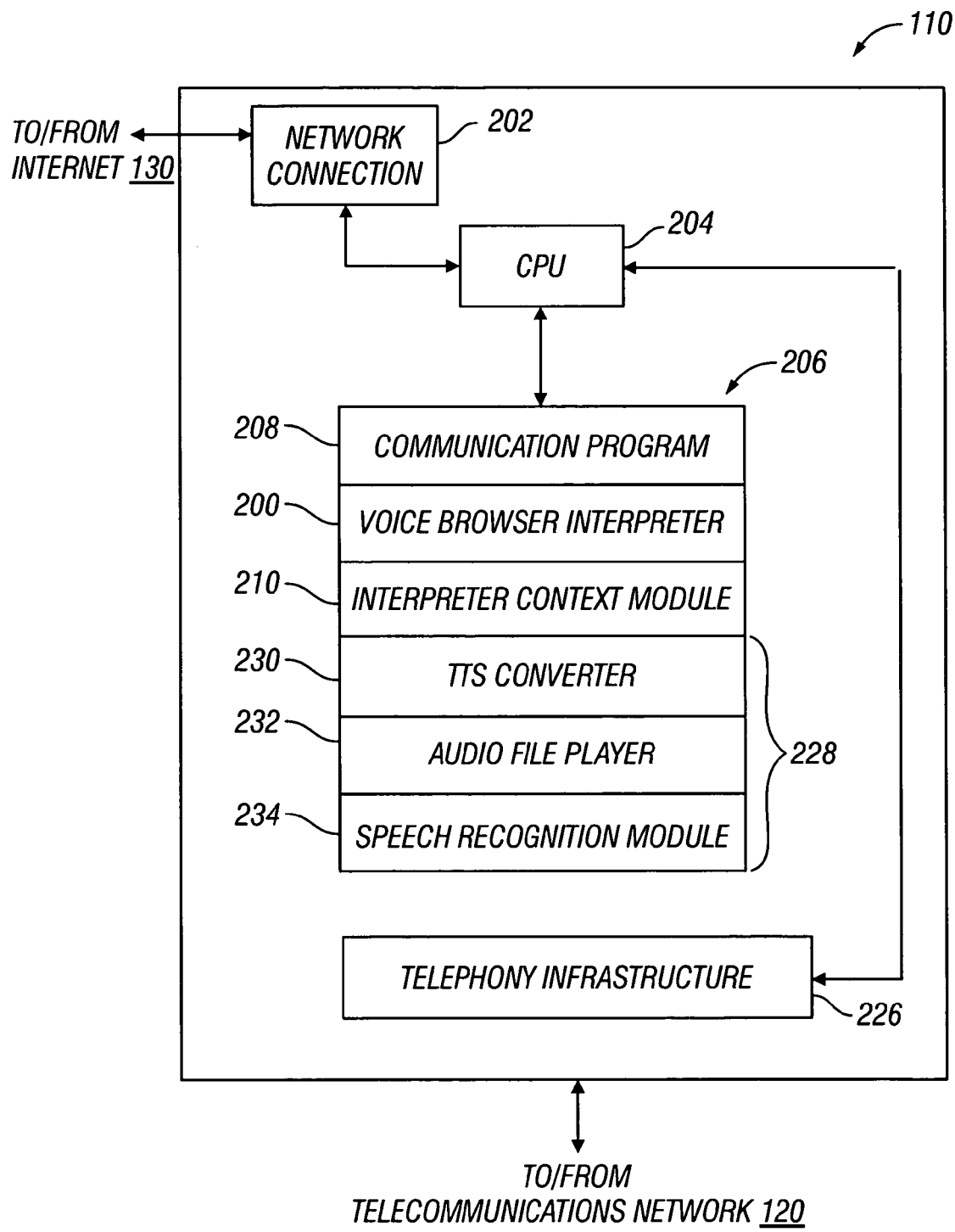
FIG. 2 shows a block diagram of a voice browser included within the system of FIG. 1.

FIG. 2 shows a block diagram of the voice browser 110. The voice browser 110 includes certain standard server computer components, including a network connection device 202 that connects to a network, e.g., the Internets, a CPU 204 and memory (primary and/or secondary) 206. The voice browser 110 also includes telephony infrastructure 226 for effecting communication with telephony-based subscriber units (e.g., the mobile subscriber unit 102 and landline telephone 104). As is described below, the memory 206 stores a set of computer programs to implement the processing effected by the voice browser 110. One such program stored by memory 206 comprises a standard communication program 208 for conducting standard network communications via the Internet 130 with the conversion server 150 and any subscriber units operating in a voice over IP mode (e.g., personal computer 106).

The memory 206 also stores a voice browser interpreter 200 and an interpreter context module 210. The voice browser interpreter 200 initiates establishment of a communication channel via the Internet 130 with the conversion server 150, response to requests. The voice browser 110 then produces browsing requests to the conversion server 150 corresponding to the requests for content submitted by the requesting subscriber unit. The conversion server 150 retrieves the requested Web or proprietary database content in response and converts the retrieved content into document files that are in VoiceXML format. The converted document files are then provided to the voice browser 110 over the established Internet communication channel and used by the voice browser interpreter 200 in carrying out a dialogue with a user of the requesting unit.

During the dialogue, the interpreter context module 210 uses conventional techniques to identify requests for help and the like which may be made by the user of the requesting subscriber unit. For example, the interpreter context module 210 may be disposed to identify predefined "escape" phrases submitted by the user in order to access menus relating to, for example, help functions or various user preferences (e.g., volume, text-to-speech characteristics).

Audio content is transmitted and received by telephony infrastructure 226 under the direction of a set of audio processing modules 228. Included among the audio processing modules 228 are a text-to-speech ("TTS") converter 230, an audio file player 232, and a speech recognition module 234. In operation, the telephony infrastructure 226 is responsible for detecting an incoming call from a telephony-based subscriber unit and for answering the call (e.g., by playing a predefined greeting). After a call from a telephony-based subscriber unit has been answered, the voice browser interpreter 200 assumes control of the dialogue with the telephony-based subscriber unit via the audio processing modules 228. In particular, audio requests from telephony-based subscriber units are parsed by the speech recognition module 234 and passed to the voice browser interpreter 200. Similarly, the voice browser interpreter 200 communicates information to telephony-based subscriber units through the text-to-speech converter 230. The telephony infrastructure 226 also receives audio signals from telephony-based subscriber units via the telecommunications network 120 in the form of DTMF signals. The telephony infrastructure 226 is able to detect and interpret the DTMF tones sent from telephony-based subscriber units. Interpreted DTMF tones are then transferred from the telephony infrastructure to the voice browser interpreter 200.

After the voice browser interpreter 200 has retrieved a VoiceXML document from the conversion server 150 in response to a request from a subscriber unit, the retrieved VoiceXML document forms the basis for the dialogue between the voice browser 110 and the requesting subscriber unit. In particular, text and audio file elements stored within the retrieved VoiceXML document are converted into audio streams in text-to-speech converter 230 and audio file player 232, respectively. When the request for content associated with these audio streams originated with a telephony-based subscriber unit, the streams are transferred to the telephony infrastructure 226 for adaptation and transmission via the telecommunications network 120 to such subscriber unit. In the case of requests for content from Internet-based subscriber units (e.g., the personal computer 106), the streams are adapted and transmitted by the network connection device 202.

The voice browser interpreter 200 interprets each retrieved VoiceXML document in a manner analogous to the manner in which a standard Web browser interprets a visual markup language, such as HTML or WML. The voice browser interpreter 200, however, interprets scripts written in a speech markup language such as VoiceXML rather than a visual markup language. In a preferred embodiment, the voice browser 110 may be realized using, consistent with the teachings herein, a voice browser licensed from, for example, Nuance Communications of Menlo Park, Calif.

Figure 3:
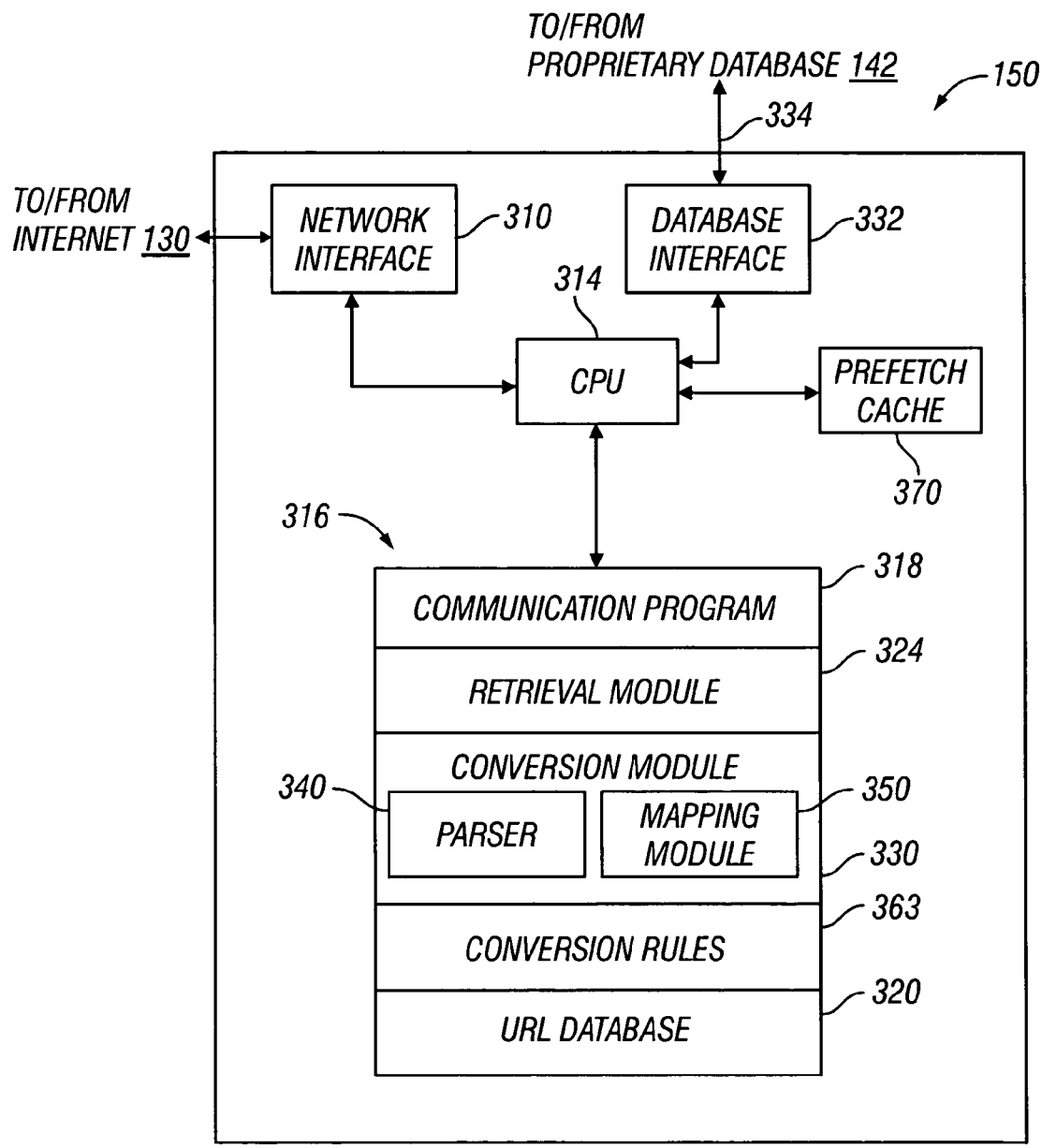
FIG. 3 is a functional block diagram of a conversion server included within the voice browser system of the present invention.

FIG. 3 shows a block diagram of the conversion server 150. As is described below, the conversion server 150 operates to convert conventional structured document formats that are formatted according to a flavor of mark-up language, such as XML or HTML into a voice mark-up language, here VoiceXML format. This conversion is generally effected by performing a predefined mapping of the syntactical elements of conventional structured documents harvested from Web servers 140 into corresponding equivalent elements contained within an XML-based file formatted in accordance with the protocol of the voice browser 110. The resultant XML-based file may include all or part of the "target" structured document harvested from the applicable Web server 140, and may also optionally include additional content provided by the conversion server 150. The target document is parsed, and identified tags, styles and content can either be replaced or removed.

The conversion server 150 may be physically implemented using a standard configuration of hardware elements including a CPU 314, a memory 316, and a network interface 310 operatively connected to the Internet 130. The memory 316 stores a standard communication program 318 to realize standard network communications via the Internet 130. The communication program 318 also controls communication occurring between the conversion server 150 and the proprietary database 142 via database interface 332. As is discussed below, the memory 316 also stores a set of computer programs to implement the content conversion process performed by the conversion module 150.

The memory 316 includes a retrieval module 324 for controlling retrieval of content from Web servers 140 and proprietary database 142 in accordance with browsing requests received from the voice browser 110. In the case of requests for content from Web servers 140, such content is retrieved via network interface 310 from Web pages formatted in accordance with protocols particularly suited to a thin client, e.g., a portable, handheld or other devices having limited display capability (e.g., WML, Compact HTML, xHTML and HDML). As discussed below, the locations or URLs of such specially formatted sites may be provided by the voice browser or may be stored within a URL database 320 of the conversion server 150. For example, if the voice browser 110 receives a request from a user of a subscriber unit for content from the "CNET" Web site, then the voice browser 110 may specify the URL for the version of the "CNET" site accessed by WAP-compliant devices (i.e., comprised of WML-formatted pages). Alternatively, the voice browser 110 could simply proffer a generic request for content from the "CNET" site to the conversion server 150, which in response would consult the URL database 320 to determine the URL of an appropriately formatted site serving "CNET" content.

The memory 316 of conversion server 150 also includes a conversion module 330 operative to convert the content collected under the direction of retrieval module 324 from Web servers 140 or the proprietary database 142 into corresponding VoiceXML documents. The retrieved content is parsed by a parser 340 of conversion module 330 in accordance with a document type definition ("DTD") corresponding to the format of such content. For example, if the retrieved Web page content is formatted in WML, the parser 340 parses the retrieved content using a DTD obtained from the applicable standards body, i.e., the Wireless Application Protocol Forum, Ltd. (www.wapforum.org) or a custom DTD, into a parsed file. A DTD establishes a set of constraints for an XML-based document; that is, a DTD defines the manner in which an XML-based document is constructed. The resultant parsed file is generally in the form of a Domain Object Model ("DOM") representation, which is arranged in a tree-like hierarchical structure composed of a plurality of interconnected nodes (i.e., a "parse tree"). The parse tree includes a plurality of "child" nodes descending downward from its root node, each of which are recursively examined and processed in the manner described below.

A mapping module 350 within the conversion module 330 traverses the parse tree and applies predefined conversion rules 363 to the elements and associated attributes at each of its nodes. In this way the mapping module 350 creates a set of corresponding equivalent elements and attributes conforming to the protocol of the voice browser 110. A converted VoiceXML document file is then generated by supplementing these equivalent elements and attributes with grammatical terms to the extent required by the protocol of the voice browser 110. This converted document file is then provided to the voice browser 110 via the network interface 310 in response to the browsing request originally issued by the voice browser 110.

The conversion module 330 is preferably a general purpose converter capable of transforming the structured document content (e.g., WML) into corresponding VoiceXML documents. The resultant VoiceXML content can then be delivered to users via any VoiceXML-compliant platform, thereby introducing a voice capability into existing structured document content. In a particular embodiment, a basic set of rules can be imposed to simplify the conversion of the structured document content into the VoiceXML format. An exemplary set of such rules utilized by the conversion module 330 may comprise the following.

1. If the structured document content (e.g., WML pages) comprises images, the conversion module 330 will discard the images and generate the necessary information for presenting the image.
2. If the structured document content comprises scripts, data or some other component not capable of being presented by voice, the conversion module 330 may generate appropriate warning messages or the like. The warning message will typically inform the user that the structured content contains a script or some component not capable of being converted to voice and that meaningful information may not be being conveyed to the user.
3. When the structured document content contains instructions similar or identical to those such as the WML-based SELECT LIST options, the conversion module 330 generates information for presenting the SELECT LIST or similar options into a menu list for audio representation. For example, an audio playback of "Please say news weather mail" could be generated for the SELCT LIST defining the three options of news, weather and mail.
4. Any hyperlinks in the structured document content are converted to reference the conversion module 330, and the actual link location passed to the conversion module as a parameter to the referencing hyperlink. In this way hyperlinks and other commands which transfer control may be voice-activated and converted to an appropriate voice-based format upon request.
5. Input fields within the structured content are converted to an active voice-based dialogue, and the appropriate commands and vocabulary added as necessary to process them.
6. Multiple screens of structured content (e.g., card-based WML screens) can be directly converted by the conversion module 330 into forms or menus of sequential dialogs. Each menu is a stand-alone component (e.g., performing a complete task such as receiving input data). The conversion module 330 may also include a feature that permits a user to interrupt the audio output generated by a voice platform (e.g., BeVocal, HeyAnita) prior to issuing a new command or input.

7. For all those events and "do" type actions similar to WML-based "OK", "Back" and "Done" operations, voice-activated commands may be employed to straightforwardly effect such actions.

8. In the exemplary embodiment the conversion module 330 operates to convert an entire page of structured content at once and to play the entire page in an uninterrupted manner. This enables relatively lengthy structured documents to be presented without the need for user intervention in the form of an audible "More" command or the equivalent.

Figure 4:
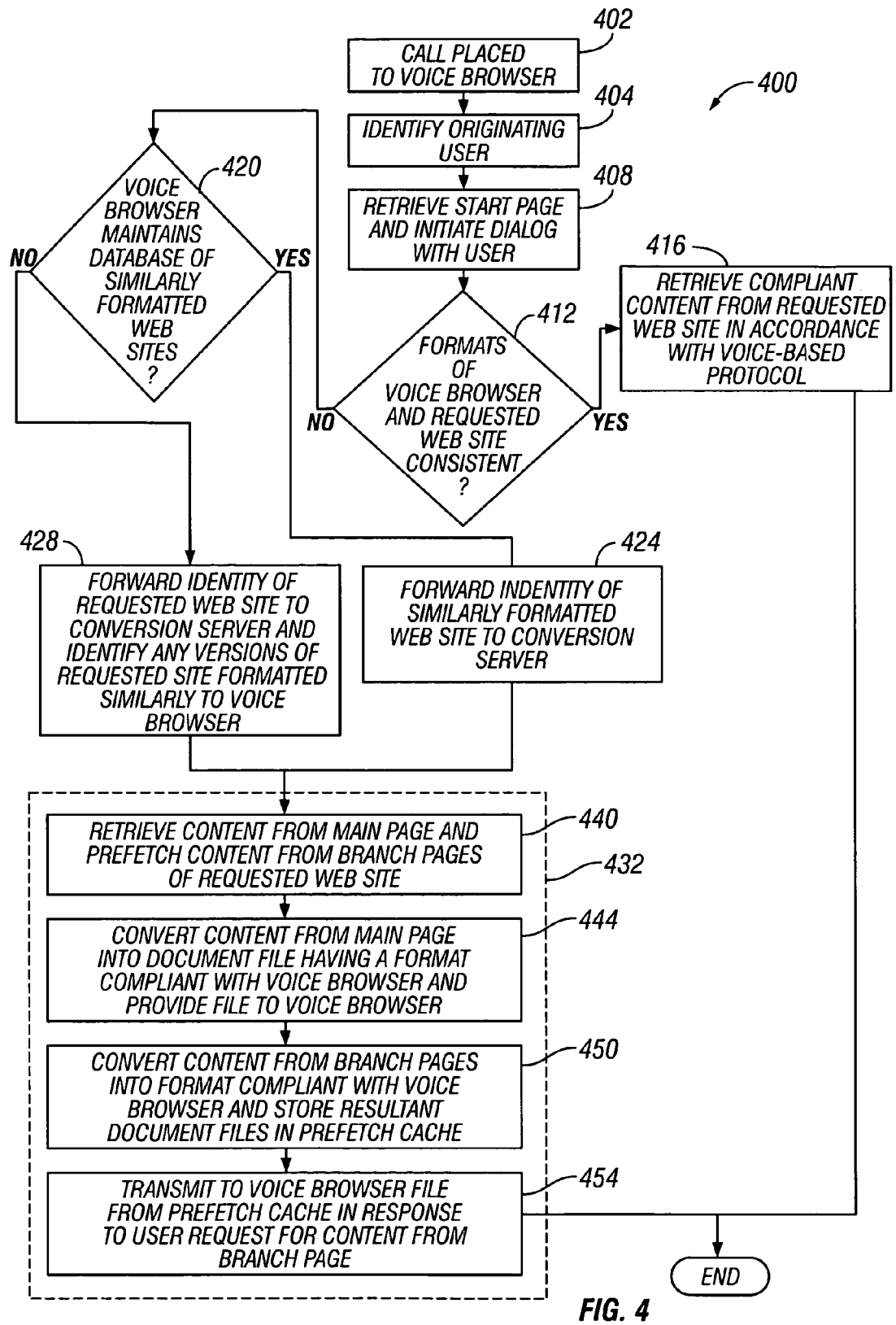
FIG. 4 is a flow chart representative of operation of the system of the present invention in furnishing Web content to a requesting user.

FIG. 4 is a flow chart representative of a process 400 executed by the system 100 in providing content from Web servers 140 to a user of a subscriber unit. At 402, the user of the subscriber unit places a call to the voice browser 110, which identifies the originating user using known techniques such as caller ID (step 404). The voice browser retrieves a start page associated with the identified user, and initiates execution of an introductory dialogue with the user such as, for example, the dialogue set forth below (408) where the designation "C" identifies the phrases generated by the voice browser 110 and conveyed to the user's subscriber unit, and the designation "U" identifies the words spoken or actions taken by such user.

C: "Welcome home, please say the name of the Web site which you would like to access"
U: "CNET dot com"
C: "Connecting, please wait . . . "
C: "Welcome to CNET, please say one of: sports; weather; business; news; stock quotes"
U: "Sports"

The manner in which the system 100 processes and responds to user input during a dialogue such as the above will vary depending upon the characteristics of the voice browser 110.

At 412, the voice browser checks to determine whether the requested Web site is of a format consistent with its own format (here, VoiceXML). If so, then the voice browser 110 may directly retrieve content from the Web server 140 hosting the requested Web site (e.g., "vxml.cnet.com") in a manner consistent with the applicable voice-based protocol (step 416). If the format of the requested Web site (e.g., "cnet.com") is inconsistent with the format of the voice browser 110, then the intelligence of the voice browser 110 influences the course of subsequent processing. Specifically, in the case where the voice browser 110 maintains a database of Web sites in formats that are consistent with its own format (420), then the voice browser 110 looks up a conforming website, and forwards the identity of such similarly formatted site (e.g., "wap.cnet.com") to the conversion server 150 via the Internet 130 in the manner described below (424). If such a database is not maintained by the voice browser 110, then in at 428 the identity of the requested Web site itself (e.g., "cnet.com") is similarly forwarded to the conversion server 150 via the Internet 130. The conversion server 150 recognizes that the format of the requested Web site (e.g., HTML) is inconsistent with the VoiceXML protocol of the voice browser 110. First, it accesses the URL database 320 in order to determine whether there exists a version of the requested Web site of a format (e.g., WML) that is more easily convertible into the protocol of the voice browser 110. Certain display protocols adapted for the limited visual displays characteristic of handheld or portable devices (e.g., WAP, HDML, iMode, Compact HTML or XML) are most readily converted into generally accepted voice-based protocols (e.g., VoiceXML). Hence the URL database 320 may include the URLs of Web sites comporting with such protocols.

Once the conversion server 150 has found a requested Web site or of a corresponding Web site of a format more readily convertible to that of the voice browser 110, the conversion server 150 retrieves and converts Web content from such requested or similarly formatted site (at 432).

The voice-browser 110 uses the same syntactical elements in its request for content from Web sites whether they are formatted in VoiceXML or not. The voice browser 110 may issue requests to VoiceXML compliant Web servers 140 using, for example, the syntactical elements goto, choice, link and submit. Voice browser 110 may request the conversion server 150 to obtain content from VoiceXML non-compliant Web sites using these same syntactical elements.

For example, the voice browser 110 could be configured to issue the following type of goto when requesting Web content through the conversion server 150:

<goto next=http://ConSeverAddress:port/Filename?URL=ContentAddress&Protocol/> where the variable ConSeverAddress within the next attribute of the goto element is set to the IP address of the conversion server 150, the variable Filename is set to the name of a conversion script (e.g., conversion.jsp) stored on the conversion server 150, the variable ContentAddress is used to specify the destination URL (e.g., "wap.cnet.com") of the Web server 140 of interest, and the variable Protocol identifies the format (e.g., WAP) of that content server. The conversion script is typically embodied in a file of conventional format (e.g., files of type ".jsp", "asp" or ".cgi"). Once this conversion script has been provided with this destination URL, Web content is retrieved from the applicable Web server 140 and converted by the conversion script into the VoiceXML format using the conversion process described below.

The voice browser 110 may also request Web content from the conversion server 150 using the choice element defined by the VoiceXML protocol. The choice element in VoiceXML is used to define potential user responses to queries posed within a menu construct. In particular, the menu construct provides a mechanism for prompting a user to make a selection, with control over subsequent dialogue with the user being changed on the basis of the user's selection. The following is an exemplary call for Web content which could be issued by the voice browser 110 to the conversion server 150 using the choice element:

<choice next="http://ConSeverAddress:port/Conversion.jsp?URL=ContentAddress&Protocol/">

(Again . . . ) The voice browser 110 may also request Web content from the conversion server 150 using the link element, which may be defined in a VoiceXML document as a child of the vxml or form constructs. An example of such a request based upon a link element is set forth below:

<link next=" Conversion.jsp?URL=ContentAddress&Protocol/">

( ) the submit element is similar to the goto element in that its execution results in procurement of a specified VoiceXML document. However, the submit element also enables an associated list of variables to be submitted to the identified Web server 140 by way of an HTTP GET or POST request. An exemplary request for Web content from the conversion server 150 using a submit expression is given below:

<submit next="htttp://http://ConSeverAddress:port//Conversion.jsp? URL=ContentAddress& Protocol method=""post" namelist="site protocol"/> where the method attribute of the submit element specifies whether an HTTP GET or POST method will be invoked, and where the namelist attribute identifies a site protocol variable forwarded to the conversion server 150. The site protocol variable is set to the formatting protocol applicable to the Web site specified by the ContentAddress variable.

The conversion server 150 operates to retrieve and convert Web content from the Web servers 140 at 432. As part of the retrieval, Web content is collected both from a "root" or "main" page of the Web site of interest, and also "prefetching" content from "child" or "branch" pages which likely to be accessed from such main page (step 440). In an implementation, the content of the retrieved main page is converted into a document file having a format consistent with VoiceXML at 444. This document file is then provided to the voice browser 110 over the Internet by the interface 310 of the conversion server 150, and forms the basis of the continuing dialogue between the voice browser 110 and the requesting user.

The conversion server 150 also converts the "prefetched" content from each branch page into VoiceXML at 450 and stores the resultant document files within a prefetch cache 370. When a request for content from such a branch page is issued to the voice browser 110 through the subscriber unit of the requesting user, the voice browser 110 forwards the request to the conversion server 150. The document file corresponding to the requested branch page is then retrieved from the prefetch cache 370 and provided to the voice browser 110 through the network interface 310. Upon being received by the voice browser 110, this document file is used in continuing a dialogue with the user of subscriber unit 102 (step 454). It follows that once the user has begun a dialogue with the voice browser 110 based upon the content of the main page of the requested Web site, such dialogue may continue substantially uninterrupted when a transition is made to one of the prefetched branch pages of such site. This approach may minimize the delay exhibited by the system 100 in responding to subsequent user requests for content once a dialogue has been initiated.

Figure 5:
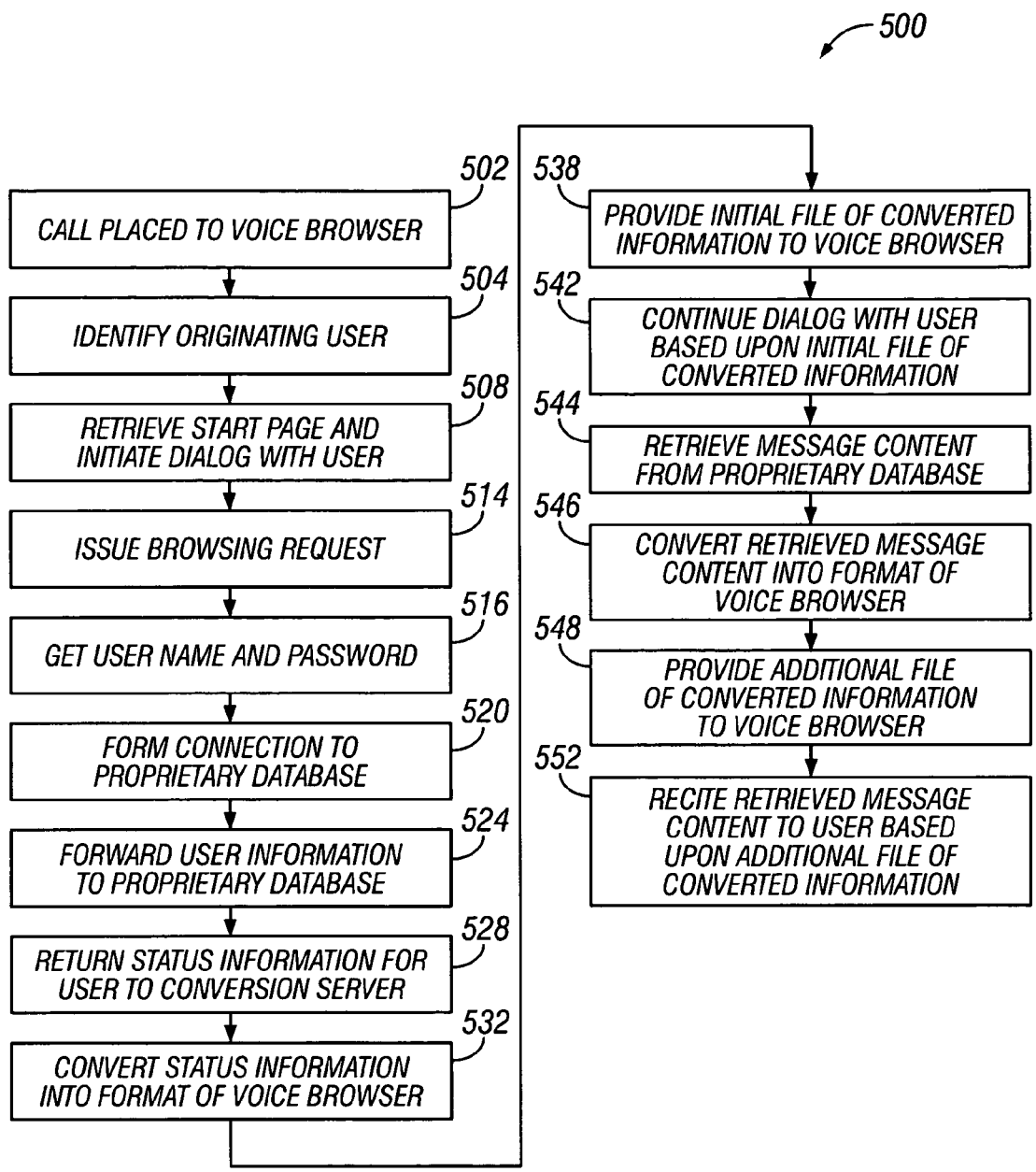
FIG. 5 is a flow chart representative of operation of the system of the present invention in providing content from a proprietary database to a requesting user.

FIG. 5 is a flow chart representative of operation of the system 100 in providing content from proprietary database 142 to a user of a subscriber unit. Proprietary database 142 is assumed to comprise a message repository included within a text-based messaging system (e.g., an electronic mail system) compliant with the ARPA standard set forth in Requests for Comments (RFC) 822, which is entitled "RFC822: Standard for ARPA Internet Text Messages" and is available at, for example, www.w3.org/Protocols/rfc822/Overview.html. At step 502, a user of a subscriber unit places a call to the voice browser 110. The originating user is identified by the voice browser 110 utilizing known techniques (step 504). The voice browser 110 then retrieves a start page associated with such user 508, and initiates execution of an introductory dialogue with the user such as, for example, the dialogue set forth below:

C: "What do you want to do?"
U: "Check Email"
C: "Please wait"

In response to the user's request to "Check Email", the voice browser 110 issues a browsing request to the conversion server 150 in order to obtain the user's email information from the proprietary database 142 (step 514). Voice browser 110 may use the VoiceXML syntactical elements goto, choice, link and submit in a substantially similar manner as that described above with reference to FIG. 4. For example, the voice browser 110 may issue the following type of goto when requesting information from the proprietary database 142 through the conversion server 150:

<goto next=http://ConServerAddress:port/email.jsp?=ServerAddress &Protocol/> where email.jsp is a program file stored within memory 316 of the conversion server 150, ServerAddress is a variable identifying the address of the proprietary database 142 (e.g., mail.V-Enable.com), and Protocol is a variable identifying the format of the database 142 (e.g., POP3).

Upon receiving such a browsing request from the voice browser 110, the conversion server 150 initiates execution of the email.jsp program file. Under the direction of email.jsp, the conversion server 150 queries the voice browser 110 for the user name and password of the requesting user (step 516) and stores the returned user information UserInfo within memory 316. The program email.jsp then calls function EmailFromUser, which forms a connection to ServerAddress based upon the Transport Control Protocol (TCP) via dedicated communication link 334 (step 520). The function EmailFromUser then invokes the method CheckEmail and furnishes the parameters ServerAddress, Protocol, and UserInfo to such method during the invocation process. Upon being invoked, CheckEmail forwards UserInfo over communication link 334 to the proprietary database 142 in accordance with RFC 822 (step 524). In response, the proprietary database 142 returns status information (e.g., number of new messages) for the requesting user to the conversion server 150 (step 528). This status information is then converted by the conversion server 150 into a format consistent with the protocol of the voice browser 110 using techniques described below (step 532). The resultant initial file of converted information is then provided to the voice browser 110 over the Internet by the network interface 310 of the conversion server 150 (step 538). Dialogue between the voice browser 110 and the user of the subscriber unit may then continue as follows based upon the initial file of converted information (step 542):

C: "You have 3 new messages"
C: "First message"

Upon forwarding the initial file of converted information to the voice browser 110, CheckEmail again forms a connection to the proprietary database 142 over dedicated communication link 334 and retrieves the content of the requesting user's new messages in accordance with RFC 822 (step 544). The retrieved message content is converted by the conversion server 150 into a format consistent with the protocol of the voice browser 110 using techniques described below (step 546). The resultant additional file of converted information is then provided to the voice browser 110 over the Internet by the network interface 310 of the conversion server 150 (step 548). The voice browser 110 then recites the retrieved message content to the requesting user in accordance with the applicable voice-based protocol based upon the additional file of converted information (step 552).

Figure 6:
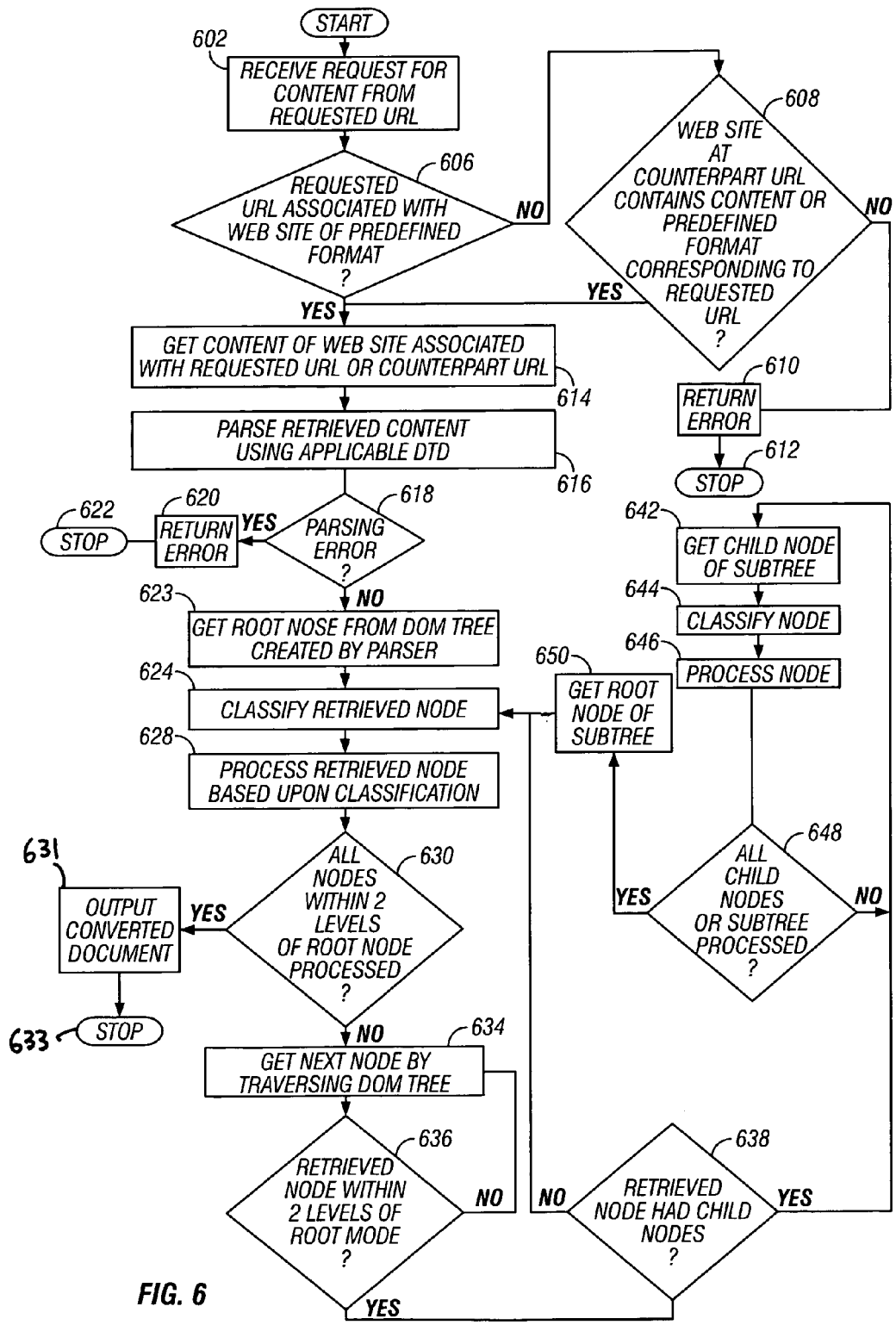
FIG. 6 is a flow chart representative of operation of the conversion server.

FIG. 6 is a flow chart showing operation of the conversion server 150. A source code listing of a top-level convert routine forming part of an exemplary software implementation of the conversion operation illustrated by FIG. 6 is contained in Appendix A in the Computer Program Listing Appendix. In addition, Appendix B in the Computer Program Listing Appendix provides an example of conversion of a WML-based document into VoiceXML-based grammatical structure in accordance with the present invention.

The conversion server 150 receives one or more requests for Web content transmitted by the voice browser 110 via the Internet 130 using conventional protocols (i.e., HTTP and TCP/IP) at 602. The conversion module 330 then determines whether the format of the requested Web site corresponds to one of a number of predefined formats (e.g., WML) readily convertible into the protocol of the voice browser 110 (step 606), e.g., a protocol where the structured portion loses minimal amounts of meaningful data during the conversion. If not, then the URL database 320 is accessed in order to determine whether a version of the requested Web site exists which is formatted consistently with one of the predefined formats (step 608). If not, an error is returned (step 610) and processing of the request for content is terminated (step 612). Once the identity of the requested Web site or of a counterpart Web site of more appropriate format has been determined, Web content is retrieved by the retrieval module 310 of the conversion server 150 from the applicable content server 140 hosting the identified Web site (step 614).

Once the identified Web-based or other content has been retrieved by the retrieval module 310, the parser 340 is invoked to parse the retrieved content using the DTD applicable to the format of the retrieved content (step 616). In the event of a parsing error (step 618), an error message is returned (step 620) and processing is terminated (step 622). A root node of the DOM representation of the retrieved content generated by the parser 340, i.e., the parse tree, is then identified (step 623). The root node is then classified into one of a number of predefined classifications (step 624). In the exemplary embodiment each node of the parse tree is assigned to one of the following classifications: Attribute, CDATA, Document Fragment, Document Type, Comment, Element, Entity Reference, Notation, Processing Instruction, Text. The content of the root node is then processed in accordance with its assigned classification in the manner described below (step 628). If all nodes within two tree levels of the root node have not been processed (step 630), then the next node of the parse tree generated by the parser 340 is identified (step 634). If not, conversion of the desired portion of the retrieved content is deemed completed (step 631) and an output file containing such desired converted content is generated and the process is stopped (step 631)

If the node of the parse tree identified in step 634 is within two levels of the root node (step 636), then it is determined whether the identified node includes any child nodes (step 638). If not, the identified node is classified (step 624). If so, the content of a first of the child nodes of the identified node is retrieved (step 642). This child node is assigned to one of the predefined classifications described above (step 644) and is processed accordingly (step 646). Once all child nodes of the identified node have been processed (step 648), the identified node (which corresponds to the root node of the subtree containing the processed child nodes) is itself retrieved (step 650) and assigned to one of the predefined classifications (step 624).

Appendix C in the Computer Program Listing Appendix contains a source code listing for a TraverseNode function which implements various aspects of the node traversal and conversion functionality described with reference to FIG. 6. In addition, Appendix D in the Computer Program Listing Appendix includes a source code listing of a ConvertAtr function, and of a ConverTag function referenced by the TraverseNode function, which collectively operate to WML tags and attributes to corresponding VoiceXML tags and attributes.

Figure 7A:
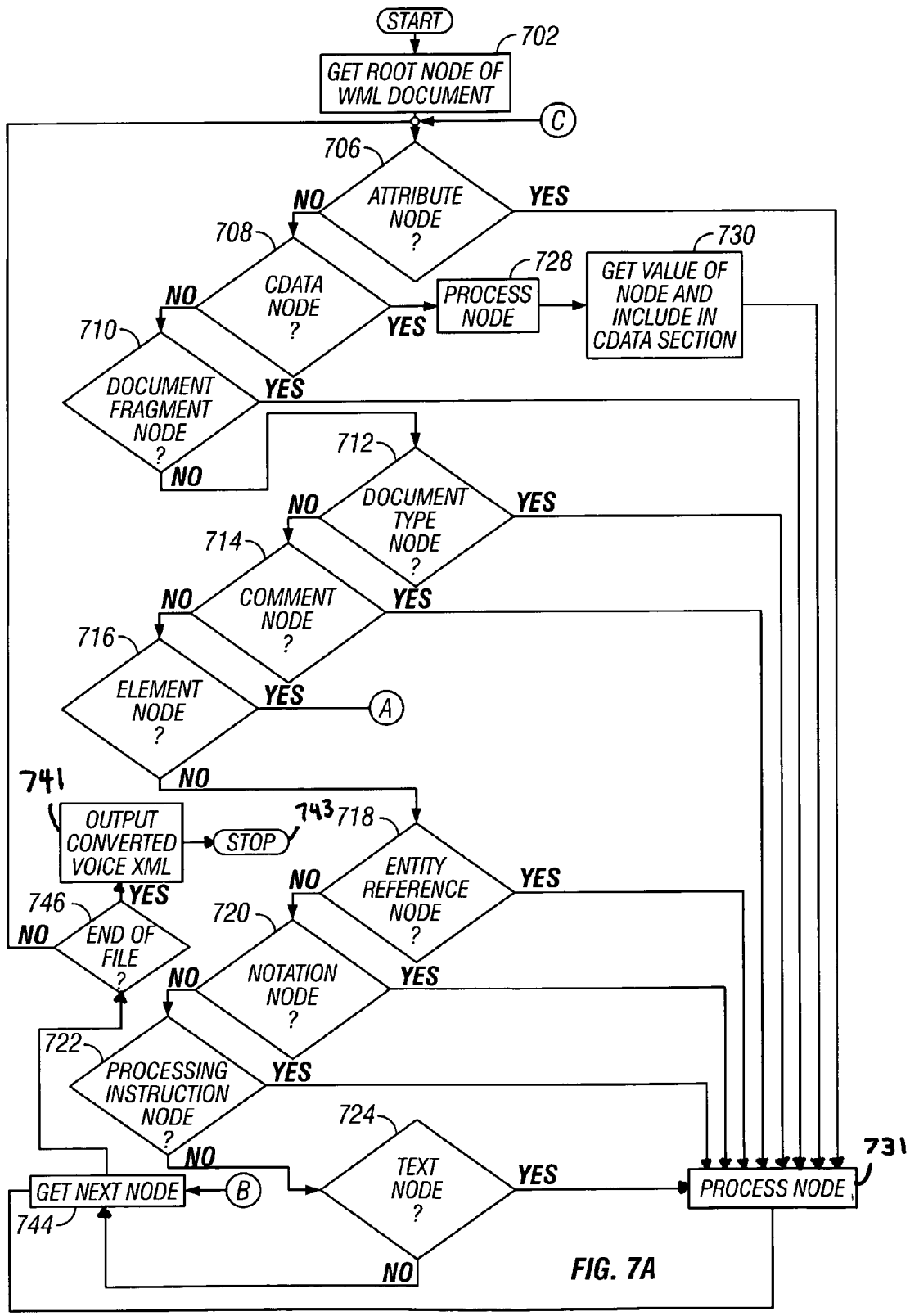
FIGS. 7A and 7B are collectively a flowchart illustrating an exemplary process for transcoding a parse tree representation of WML-based document into an output document comporting with the VoiceXML protocol.
Figure 7B:
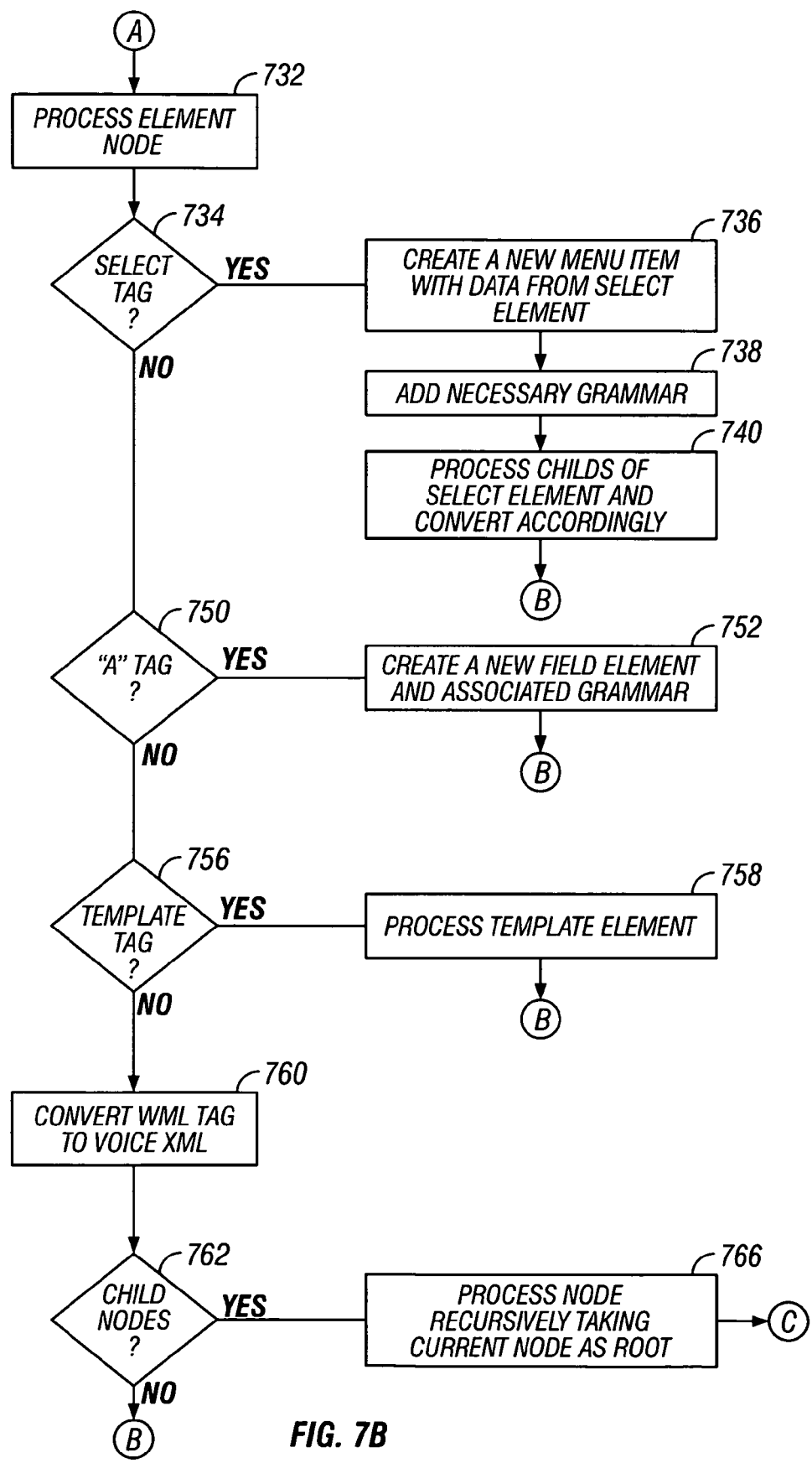

FIGS. 7A and 7B are collectively a flowchart illustrating an exemplary process for transcoding a parse tree representation of an WML-based document into an output document comporting with the VoiceXML protocol. Although FIG. 7 describes the transcoding process with specific reference to the WML and VoiceXML protocols, the process is also readily applicable to conversion between other visual-based and voice-based protocols. In 702, a root node of the parse tree for the target WML document to be transcoded is retrieved. The type of the root node is then determined and, based upon this identified type, the root node is processed accordingly (step 731). Specifically, the conversion process determines whether the root node is an attribute node (step 706), a CDATA node (step 708), a document fragment node (step 710), a document type node (step 712), a comment node (step 714), an element node (step 716), an entity reference node (step 718), a notation node (step 720), a processing instruction node (step 722), or a text node (step 724).

```
WML-Based CDATA Block
<?xml version="1.0" ?>
<!DOCTYPE wml PUBLIC "-//WAPFORUM//DTD WML 1.1//EN"
"http://www.wapforum.org/DTD/wml_1.1.xml">
<wml>
  <card>
    <p>
      <![CDATA[
      .....
      .....
      .....
      ]]>
    </p>
  </card>
</wml>
VoiceXML Representation of CDATA Block
<?xml version="1.0" ?>
<vxml>
  <form>
    <block>
      <![CDATA[
      .....
      .....
      .....
      ]]>
    </block>
  </form>
</vxml>
```

If it is established that the root node is an element node (step 716), then processing proceeds as depicted in FIG. 7B (step 732). If a Select tag is found to be associated with the root node (step 734), then a new menu item is created based upon the data comprising the identified select tag (step 736). Any grammar necessary to ensure that the new menu item comports with the VoiceXML protocol is then added (step 738).

In accordance with the invention, the operations defined by the WML-based Select tag are mapped to corresponding operations presented through the VoiceXML-based Menu tag. The Select tag is typically utilized to specify a visual list of user options and to define corresponding actions to be taken depending upon the option selected. Similarly, a Menu tag in VoiceXML specifies an introductory message and a set of spoken prompts corresponding to a set of choices. The Menu tag also specifies a corresponding set of possible responses to the prompts, and will typically also specify a URL to which a user is directed upon selecting a particular choice. When the grammatical structure defined by a Menu tag is visited, its introductory text is spoken followed by the prompt text of any contained Choice tags. A grammar for matching the "title" text of the grammatical structure defined by a Menu tag may be activated upon being loaded. When a word or phrase which matches the title text of a Menu tag is spoken by a user, the user is directed to the grammatical structure defined by the Menu tag.

The following exemplary code corresponding to a WML-based Select operation and a corresponding VoiceXML-based Menu operation illustrate this conversion process. Each operation facilitates presentation of a set of four potential options for selection by a user: "cnet news", "V-enable", "Yahoo stocks", and "Wireless Knowledge"

```
Select operation
<select ivalue="1" name="action">
    <option title="OK" onpick="http://cnet.news.com>
    Cnet news</option>
    <option title="OK" onpick="http://www.v-enable.com>
    V-enable/option>
    <option title="OK" onpick="http://stocks.yahoo.com>
    Yahoo stocks</option>
    <option title="OK" onpick="http://www.wirelessknowledge.com">
    Visit Wireless Knowledge</option>
</select>
Menu operation
<menu id="mainMenu" >
    <prompt>Please choose from <enumerate/> </prompt>
        <choice
        next="http://server:port/Convert.jsp?url=http://cnet.new
        s.com"> Cnet news </choice>
        <choice
        next="http://server:port/Convert.jsp?url=http://www.v-
        enable.com">V-enable</choice>
        <choice next="http://server:port/Convert.jsp?url=
        http://stocks.yahoo.com"> Yahoo stocks</choice>
        <choice next="http://server:port/Convert.jsp?url=
        http://www.wirelessknowledge.com">Visit Wireless
        Knowledge</choice>
</menu>
```

The main menu may serve as the top-level menu which is heard first when the user initiates a session using the voice browser 110. The Enumerate tag inside the Menu tag automatically builds a list of words from identified by the Choice tags (i.e., "Cnet news", "V-enable", "Yahoo stocks", and "Visit Wireless Knowledge". When the voice browser 110 visits this menu, The Prompt tag then causes it to prompt the user with following text "Please choose from Cnet news, V-enable, Yahoo stocks, Visit Wireless Knowledge". Once this menu has been loaded by the voice browser 110, the user may select any of the choices by speaking a command consistent with the technology used by the voice browser 110. For example, the allowable commands may include various "attention" phrases (e.g., "go to" or "select") followed by the prompt words corresponding to various choices (e.g., "select Cnet news"). After the user has voiced a selection, the voice browser 110 will visit the target URL specified by the relevant attribute associated with the selected choice. In the above conversion, the URL address specified in the onpick attribute of the Option tag is passed as an argument to the Convert.jsp process in the next attribute of the Choice tag. The Convert.jsp process then converts the content specified by the URL address into well-formatted VoiceXML. The format of a set of URL addresses associated with each of the choices defined by the foregoing exemplary main menu are set forth below:

Cnet news--->
http://HybridPlatform:port/Convert.jsp?url=http://cnet-.news.com
V-enable--->
http://HybridPlatform:port/Convert.jsp?url=http://www.v-enable.com
Yahoo stocks--->
http://HybridPlatform:port/Convert.jsp?url=http://stocks.yahoo.com
Visit Wireless Knowledge-->
http://Hybridplatform:port/Convert.jsp?url=http://www-.wirelessknowle dge.com Referring again to FIG. 7B, any "child" tags of the Select tag are then processed as described above with respect to the original "root" node of the parse tree and accordingly converted into VoiceXML-based grammatical structures (step 740). Upon completion of the processing of each child of the Select tag, the information, associated with the next unprocessed node of the parse tree is retrieved (step 744). To the extent an unprocessed node was identified in step 744 (step 746), the identified node is processed in the manner described above beginning with step 706. Otherwise, a converted voice XML is output (step 741) and the process stopped (step 743).

Again directing attention to step 740, an XML-based tag (including, e.g., a Select tag) may be associated with one or more subsidiary "child" tags. Similarly, every XML-based tag (except the tag associated with the root node of a parse tree) is also associated with a parent tag. The following XML-based notation exemplifies this parent/child relationship:

```
<parent>
    <child1>
        <grandchild1> ..... </grandchild1>
    </child1>
    <child2>
        .....
    </child2>
</parent>
```

In the above example the parent tag is associated with two child tags (i.e., child1 and child2). In addition, tag child1 has a child tag denominated grandchild1. In the case of exemplary WML-based Select operation defined above, the Select tag is the parent of the Option tag and the Option tag is the child of the Select tag. In the corresponding case of the VoiceXML-based Menu operation, the Prompt and Choice tags are children of the Menu tag (and the Menu tag is the parent of both the Prompt and Choice tags).

Various types of information are typically associated with each parent and child tag. For example, list of various types of attributes are commonly associated with certain types of tags. Textual information associated with a given tag may also be encapsulated between the "start" and "end" tagname markings defining a tag structure (e.g., "</tagname>"), with the specific semantics of the tag being dependent upon the type of tag. An accepted structure for a WML-based tag is set forth below:

```
<tagname attribute1=value attribute2= value .....> text
information </tagname>.
```

Applying this structure to the case of the exemplary WML-based Option tag described above, it is seen to have the attributes of title and onpick. The title attribute defines the title of the Option tag, while the option attribute specifies the action to be taken if the Option tag is selected. This Option tag also incorporates descriptive text information presented to a user in order to facilitate selection of the Option.

If an "A" tag is determined to be associated with the element node (step 750), then a new field element and associated grammar are created (step 752) in order to process the tag based upon its attributes. Upon completion of creation of this new field element and associated grammar, the next node in the parse tree is obtained and processing is continued at step 744 in the manner described above. An exemplary conversion of a WML-based A tag into a VoiceXML-based Field tag and associated grammar is set forth below:

---

WML File With "A" tag
```
<?xml version="1.0"?>
<!DOCTYPE wml PUBLIC "-//WAPFORUM//DTD WML 1.1//EN"
"http://www.wapform.org/DTD/wml 1.1.xml">
<wml>
    <card id="test" title="Test">
        <p>This is a test</p>
        <p>
            <A title="Go" href="test.wml"> Hello </A>
        </p>
    </card>
</wml>
```
Here "A" tag has
 1. Title = "go"
 2. href = "test.wml"
 3. Display on screen: Hello [the content between <A ..> </A> is displayed on screen]

Converted VXML with Field Element
```
<?xml version="1.0"?>
<vxml>
    <form id="test">
    <block>This is a test</block>
    <block>
        <field name="act">
            <prompt> Please say Hello or next </prompt>
            <grammar>
            [ Hello Next ]
            </grammar>
            <filled>
                <if cond="act == 'Hello' ">
                    <goto next="test.wml" />
                </if>
            </filled>
        </field>
    </block>
    </card>
</vxml>
```

---

In the above example, the WML-based textual representation of "Hello" and "Next" are converted into a VoiceXML-based representation pursuant to which they are audibly presented. If the user utters "Hello" in response, control passes to the same link as was referenced by the WML "A" tag. If instead "Next" is spoken, then VoiceXML processing begins after the "</field>" tag.

If a Template tag is found to be associated with the element node (step 756), the template element is processed by converting it to a VoiceXML-based Link element (step 758). The next node in the parse tree is then obtained and processing is continued at step 744 in the manner described above. An exemplary conversion of the information associated with a WML-based Template tag into a VoiceXML-based Link element is set forth below.

---

Template Tag
```
<?xml version="1.0"?>
<!DOCTYPE wml PUBLIC "-//WAPFORUM//DTD WML 1.1//EN"
"http://www.wap/wml 1.1.xml">
<wml>
    <template>
        <do type="options" label="Main">
            <go href="next.wml"/>
        </do>
    </template>
    <card>
        <p> hello </p>
    </card>
</wml>
```
Link Element
```
<?xml version="1.0"?>
<vxml>
    <link caching="safe" next="next.wml">
        <grammar>
            [ (Main) ]
        </grammar>
    </link>
    <form>
        <block> hello </block>
    </form>
</wml>
```

---

In the event that a WML tag is determined to be associated with the element node, then the WML tag is converted to VoiceXML (step 760).

If the element node does not include any child nodes, then the next node in the parse tree is obtained and processing is continued at step 744 in the manner described above (step 762). If the element node does include child nodes, each child node within the subtree of the parse tree formed by considering the element node to be the root node of the subtree is then processed beginning at step 706 in the manner described above (step 766).

Multi-Mode Information Retrieval System

Figure 8:
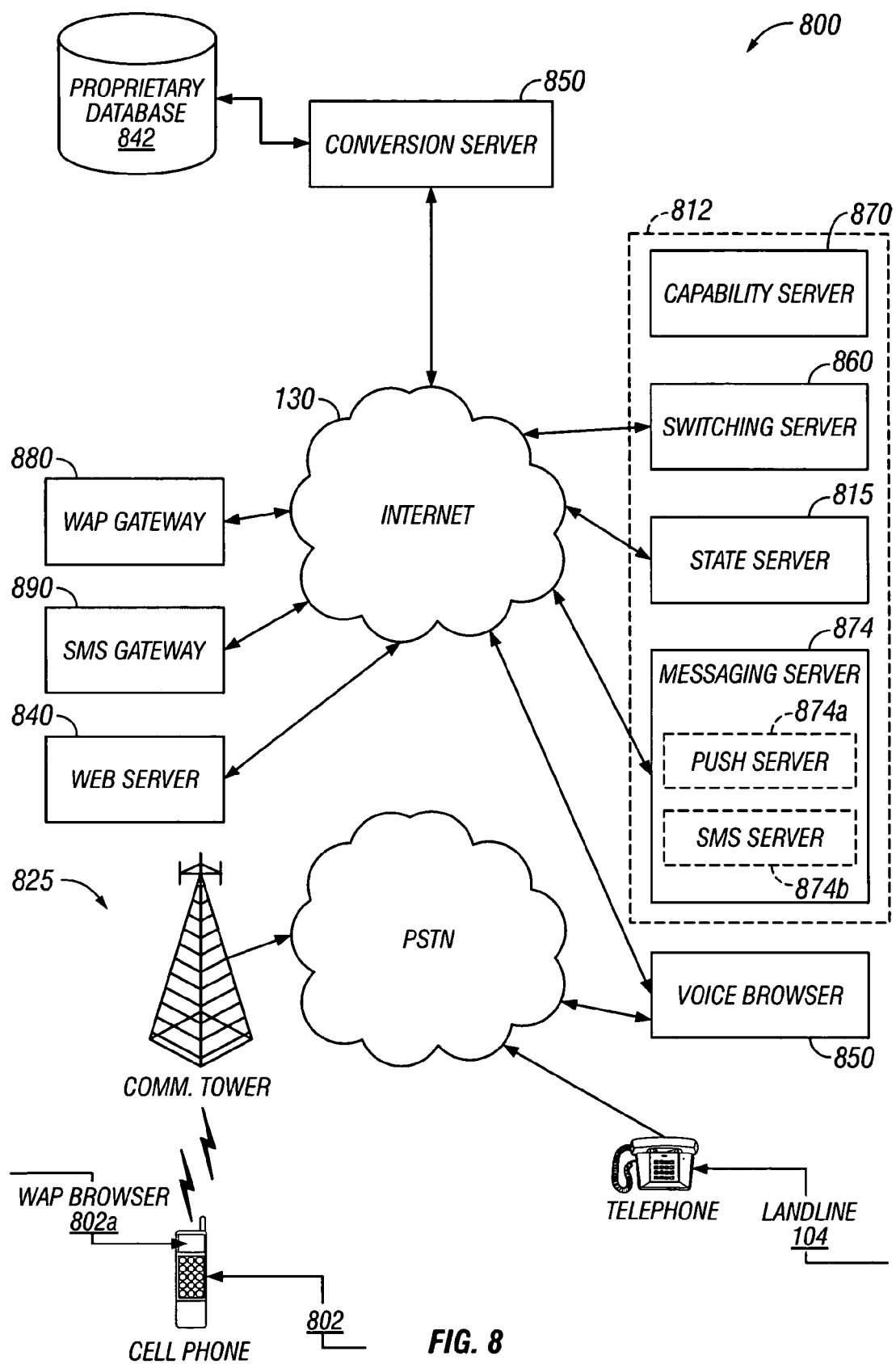
FIG. 8 provides a schematic diagram of a voice-based system for accessing Web content within which the present invention may be incorporated.

FIG. 8 provides a schematic diagram of a voice-based system 800 for accessing Web content, which includes a multi-mode platform 812 incorporating a switching server 860, a state server 815, a device capability server 870 and a messaging server 874. The messaging server 874 includes a push server 874*a* and SMS server 874*b*. The system 800 also includes telephonic subscriber unit 802 with voice capabilities, display capabilities, messaging capabilities and/or WAP browser capability in communication with a voice browser 850. As shown, the system 800 further includes a WAP gateway 880 and/or a SMS gateway 890. In operation, data content from the web server 840 or any other source of content is received either in voice form through the voice browser 850 or in visual form through the WAP gateway 880/SMS gateway 890 into and provided to the telephonic subscriber unit 802 via a wireless network 825.

Voice browser 850 executes dialogues with a user of the subscriber unit 802 using voice mode based on document files formatted according to VoiceXML, although any other speech "mark-up" language may be used. The document file requested may contain additional special tags, called "Multi-modal tags". These Multi-modal tags are not part of VoiceXML standard, but rather are used for making the content Multi-modal, i.e., browsable in one of multiple formats. The tag includes information that allows the voice browser 850 to switch the context from voice mode to visual mode using the switching server 860, the messaging server 824 and the device capability server 870. Either or both voice and visual mode may be active at any time, depending on the kind of tag used in the document.

The voice browser 850 generally obtains such document files through the multi-mode platform 210. To operate in VoiceXML, the multi-mode platform 812 may interpret the Multi-modal tags and convert them into VoiceXML. The multi-mode platform 812 then provides the converted Multi-modal document file to the voice browser 850, which then uses this file to effect a dialogue conforming to the applicable voice-based protocol, with the user of subscriber unit 802.

This same content may be used to allow the WAP browser 802a to execute dialogues with a user of the subscriber unit 802 using visual mode on the basis of document files comporting with a known visual mark-up language, here WML, through the WAP gateway 880. The document file requested may contain the Multi-modal tags, again which are not part of the visual mark-up-language specification, but which are useful in rendering the content Multi-modal. The Multi-modal tag allows the WAP browser 802a to switch the context from visual mode to voice mode using the switching server 860 and the state server 815. Either both voice and visual mode are active at the same time or just one mode is active at a time depending on the kind of tag used. The WAP browser 802a generally obtains such document files through the multi-mode platform 812 via the WAP gateway 880. The multi-mode platform 812 does the necessary interpretation of the Multi-modal tags and converts them in accordance with WML. The multi-mode platform 812 then provides the converted Multi-modal document file to the WAP browser 802a, which then uses this file to effect a dialogue in WML with the user of subscriber unit 802.

As mentioned above, the Multi-modal content integrates both visual (e.g. WML, text, iMode) content and voice (e.g. VoiceXML) content. The user has the option of either listening to the content (e.g. VoiceXML) over a voice channel, and/or the user can see the content (e.g. WML) over the data channel (e.g., WAP, SMS). In a realistic scenario, the user may browse visual content (e.g., WML). During the browsing, the user may say or click on 'listen' at any time and the WAP browser 802a will switch the context to voice using the switching server 160. This allows the user to communicate with the same content, in voice form, through the voice browser 850. Similarly, while listening to any voice content (e.g., VXML) the user can say or click on 'see' causing the voice browser 850 to switch the context to visual using the switching server 160. The user then communicates with the same content in the visual form through the WAP browser 802a.

The user can also have an active voice session which may be enhanced using the visuals coming from the data channel at the same time. An example could be an email application, where user is listening to its email subjects. The multi-mode platform pushes the email headers onto the display screen of subscriber unit 802. The user can say the number of the email it wants to listen to, by looking at the email subjects displayed on the screen using the visual mode and the corresponding email will be played by the voice browser 850 using the voice channel.

The following Multi-modal tags can be used in the voice markup language (e.g., VoiceXML) in order to facilitate making the voice content Multi-modal;

Switch

A <switch> tag is provided in order to allow a user to switch the context from current VXML to visual mode. The switch tag contains the URL that the user wants to see when it switches the mode. The switch tag is not processed by the voice player provider (e.g., HeyAnita), but is internally processed by the multi-mode platform. The multi-mode platform internally calls a JSP/Servlet in order to process the <switch> tag.

Syntax
<switch url="wmlfile|vxmlfile|HDMLfile|iMode|plaintext file" text="any text" title="title"/>

| Attribute | Description |
|---|---|
| url | is URL address of the any visual based content such as WML. HDML or any voice based content such as VXMLthat you want to see. The URL could even point to plain text. |
| Text | Allows the developer to send the inline text to the phone. |
| Title | Is the title of the link, default is "NewAlert"cte |

Note: Either url attribute or text attribute is present.

One of them should always be present.

```
<if cond="show" >
  <switch url ="http://wap.cnet.com/news.wml " title ="news" />
</if>
The multi-mode platform will translate the switch in the following way:
< if cond="show" >
  <goto
  next ="http://www.v-
  enable.com/SwitchContextToVoice.jsp?phoneNo=session.telephone.ani
  &
  url=http://wap.cnet.com/news.wml &title=news" />
</if>
```

In one embodiment, switching is carried out by cancelling the current voice call initiating a data call is automatically initiated to start the visual session.

The SwitchContextToVoice.jsp initiates a client request to switching server 860 in order to switch the context from voice to visual.

The SwitchContextToVisual.jsp first detects the device capability of the subscriber unit 802 using the device capability server 870 to determine if the subscriber unit 802 is capable of accepting a push message or a SMS message. The SwitchContextToVisual.jsp uses the session.telephone.ani to get the details of the user. The detail about the properties of the subscriber unit 802 is registered with the multi-mode platform before the user can use the services of the multi-mode platform. The session.telephone.ani, which is also the phone number, is used as the key to identify a user. All WAP-enabled subscriber phones accept push messages where you can send a WML link along with the push message. SMS enabled phones accept SMS messages and it is possible to attach a call back number along with the SMS message.

If the subscriber unit 802 is WAP-enabled and thus capable of accepting push messages, then SwitchContextToVisual.jsp requests the messaging server 824 which further requests the push server 200a and sends a push message to the subscriber unit 802. The push message contains a URL link of another JSP/Servlet HybridWML.jsp. If the url attribute is present then the HybridWML.jsp checks if the URL link in the switch tag, representing the user's requested content, is in appropriate format (WML) for the browser to display it. The content specified by the URL link in the switch tag is converted into Multi-Mode WML and then pushes the Multi-Mode WML content into the WAP browser. SwitchContextToVisual.jsp uses another JSP/Servlet push.jsp in order to push the Multi-Mode WML link to the WAP browser using push protocol. Else if text attribute is present then HybridWML.jsp converts the inline text present in the text attribute into a valid hybridWML file suitable for viewing by the WAP browser.

Else if the subscriber unit 802 is SMS-based, then SwitchContextToVisual.jsp converts the URL present (if present) in the switch tag into a plain text message. SwitchContextToVisual.jsp then requests the messaging server 824, which further requests the SMS server 874b and sends the plain text to the subscriber unit 802 by using the SMS server 874b. The SMS server 874b also attaches a call back number of the voice player (e.g., HeyAnita) so that the user can listen to the plain text. If the text attribute is present then the inline text is directly pushed on the screen of the subscriber unit 802 as an SMS message.

One technique for determining if the subscriber unit 802 is "push-capable" or is "SMS-capable" is as follows. As part of the multi-mode platform registration process, users are allowed to register a predetermined web site (e.g., www.v-enable.org). In the registration process, the user provides the phone number that will be used to access the multi-mode platform. When the web registration is complete, a test SMS message is sent to the user's phone using the SMS server 874b. SMS server uses the SMS APIs provided by the service provider (Cingular, Nextel, Sprint etc). If the SMS function returns success, then it is known that the phone is capable of receiving SMS. Else it is concluded that the phone does not have SMS capability. This information is then stored in the user capability database.

Figure 10:
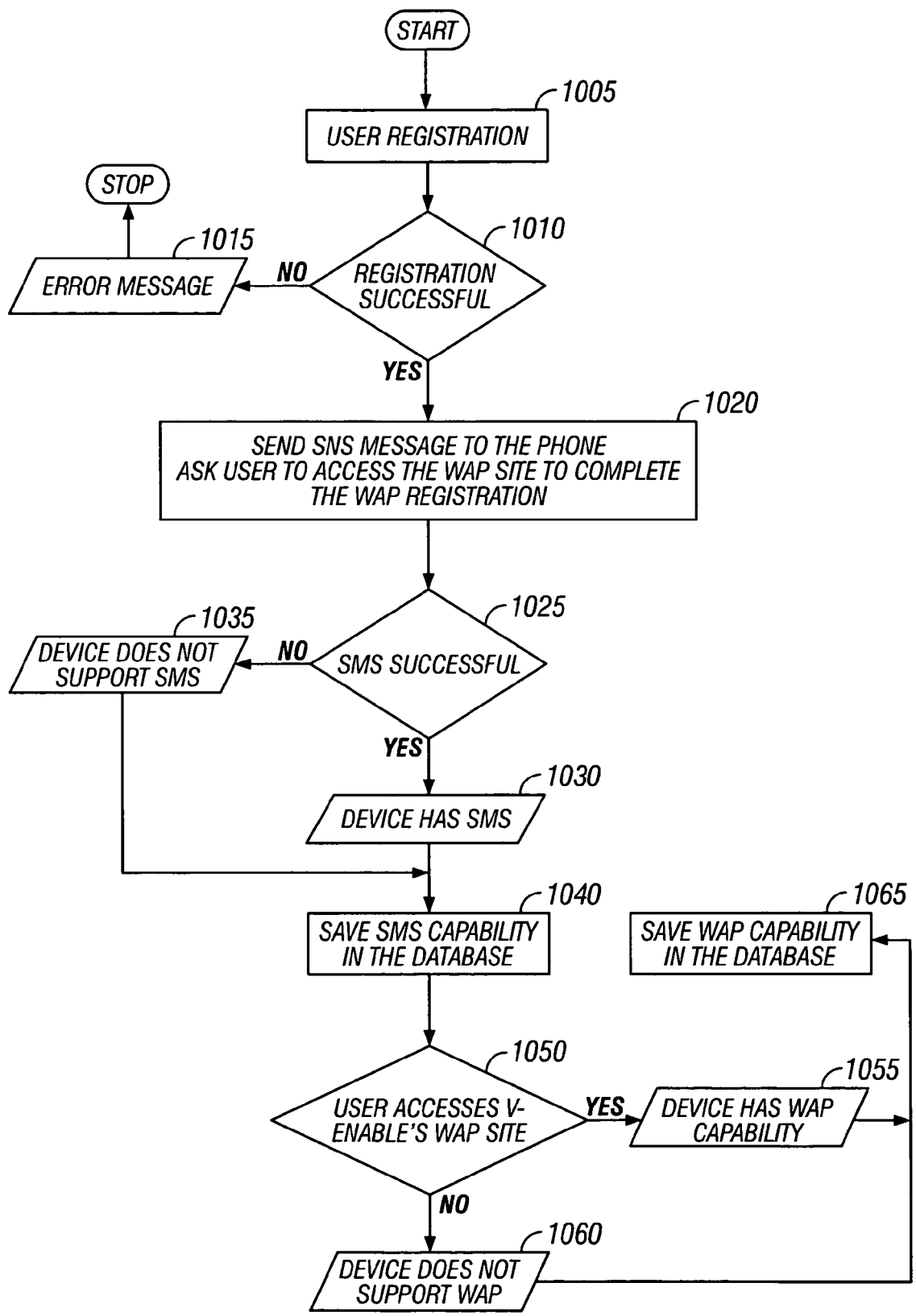
FIG. 10 is a flow chart representative of a registration process involving the inventive multi-mode platform.

In order to find out whether a phone has WAP capability, the multi-mode platform uses a two-step registration shown in the flowchart of FIG. 10. The user first registers using the web registration at 1005. 1010 detects if the registration was successful; if not an error message is sent at 1015.

The multi-mode platform then informs the user by SMS to access a predetermined WAP-based web site with the phone, if the phone has WAP capabilities at 1020. 1025 determines if SMS was successful, and determines if the device does (1030) or does not (1035) support SMS. This result is saved at 1040. If the user successfully accesses the predetermined WAP-based site at 1050, then the device is identified as WAP-capable at 1055. If the user does not have WAP capability, then it cannot access the predetermined WAP site and the device is identified as not being WAP-capable at 1060. This information is also stored in the user capability database at 1065. Later, the multi-mode platform uses this capability database to find out whether the device is SMS capable, WAP capable or not.

Show
<show text="" url="" next=" VOICE_URL">

| Attribute | Description |
| --- | --- |
| Text | text is the inline text message the developer want to send on the phone |

-continued

| Attribute | Description |
| --- | --- |
| url | url is the link the developer wants to see on the screen. |
| Next | next is the url where the control flow begin once the data is sent to the phone. |

Note:
Either an url attribute or a text attribute is present, and one of them should always be present.

The SHOW TAG leverages the simultaneous dual channel capability of 2.0/2.5/3.0G phones. For example, SMS and voice sessions can be simultaneously active in a 2.0G phone. When the SHOW TAG is executed, the current voice session remains active, whereas the SWITCH TAG disconnects the voice session after starting the data session. The multi-mode platform 812 provides the necessary synchronization and state management needed to coordinate between the voice and data channel being active at the same time.

Following is a simple email example which demonstrates the multi modal application on a 2G phone. The showtestemail.vxml uses the SHOW tag to send email headers to the user phone. After sending the headers to the phone, the voice session is redirected to the email.vxml. The email.vxml file represents the value of the next attribute in the SHOW tag and prompts the user to say a desired header number. The email.vxml then plays the email requested by the user. An advantage of the SHOW tag is that it allows a 2G phone to have simultaneous access to voice as well visual content using SMS. The SHOW tag can be used in 2.0G to 2.5/3.0G phones.

```
File: showtestemail.vxml
<?xml version="1.0"?>
<vxml version="1.0">
<form id ="showtest">
   <block>
      <prompt>
         Email. This demonstrates the show tag. </prompt>
      <show text ="1:Hello 2:Happy New Year 3:Meeting postponed"
         next ="http://www.v-enable.org/appl/email.vxml"/>
   </block>
</form>
</vxml>
```
The multi-mode platform will translate the above showtestemail.vxml as
```
<?xml version="1.0"?>
<vxml version="1.0">
<form id ="showtest">
   <block>
      <prompt>
         Email. This demonstrates the show tag. \
      </prompt>
      <goto next="http://www.v-enable.org/ShowText.jsp?
         phoneNo=session.telephone.ani&
         SMSText=1:Hello 2:Happy New Year 3:Meeting postponed&
         next =http://www.v-enable.org/appl/email.vxml/>
   </block>
</form>
</vxml>
File: email.vxml
<?xml version="1.0"?>
<vxml version="1.0">
<form id ="address">
<property name ="bargein" value="false"/>
   <field name="sel">
      <prompt bargein="false">
      Please say the number of the email header you want to
      listen.
      </prompt>
      <grammar>
         [one two three]
```

```
        </grammar>
        <noinput>
            <prompt> I am sorry I din't hear anything </prompt>
            <reprompt/>
        </noinput>
    </field>
    <filled>
        <if cond="sel=='one' ">
            <goto next=http://www.v-enable.org/email/one.vxml/>
            <elseif cond="sel=='two' "/>
            <goto next=http://www.v-enable.org/email/two.vxml/>
            <elseif cond="sel=='three' "/>
            <goto next=http://www.v-enable.org/email/three.vxml/>
        </if>
    </filled>
</form>
</vxml>
```

The ShowText.jsp initiates a client request to messaging server 824. The messaging server 824 in turn passes the request to SMS server 874b, realizing that a SMS has to be sent. The SMS server 874b sends the SMS message to the user using the phone number. The SMS server 874b can use two different approaches for sending SMS to the subscriber unit 802: 1) SMTP protocol.

The SMTP (Simple Mail Transfer Protocol) is the protocol often used for sending emails over Internet. The SMTP protocol is used to send the SMS message as an email to the subscriber. The email address for the subscriber 802 is provided by the service providers such as SprintPCS, Cingular etc. For example, a SprintPCS telephone number xxxyyyzzzz will have email address as xxxyyyzzzz@messaging.sprintpcs.com. Any email sent to this address will be delivered to the subscriber unit 802 as an SMS message by the SprintPCS messaging gateway (SMSC).

2) Using SMPP protocol—the SMPP (Short Message Peer to Peer) protocol is an industry standard that defines the communication between the SMSC (Short Message Service Center) gateway and the external entities such as SMS server 874b for sending SMS messages to the subscriber units such as 802. The SMPP protocol gives you more control over the SMS message sent. The status of the SMS sent could be queried and action could be taken accordingly, for example, a retransmission is done if the subscriber has not received the SMS message.

Once the user successfully receives the message, the SMS server directs the current active voice call, to play the VoiceXML file specified in the next attribute of the show tag. In this case the file name is email.vxml.

As mentioned above, following are the Multi-modal tags, which can be used in the visual markup language (e.g., WML) in order to make the visual content multi-modal.

Switch

A <switch> tag is provided for WML developers in order to allow the user of the subscriber unit 802 to switch the context from current visual mode to voice mode. The switch tag should have a URL in it that the user wants to listen when it switches the mode. The switch tag is not processed by the WAP browser, but is internally processed by the multi-mode platform. The multi-mode platform internally calls a JSP/Servlet in order to process the <switch> tag. The developer can use the <switch> tag whenever the developer wants action to be switched to voice mode.

Syntax
<switch
    url="wmlfile|vxmlfile|HDMLfile|iMode|plaintext|audiofiles"
    text-"any text"/>

| Attribute | Description |
|-----------|-------------|
| url | is URL address of the any visual based content such as WML, HDML etc. or any voice based content such as VXML that you want to listen. The URL could even point to plain text or audio formats. Non-Voice formats are automatically converted into valid voice formats (VoiceXML). |
| Text | allows the developers to listen to inline text over the voice channel. |

Note:
Either url attribute or text attribute is present.
One of them should always be present.

The application developer while using the visual markup language such as WML would write something like this:

```
<wml>
    <card title="News Service">
        <p>
            Cnet news
        </p>
        <do type="options" label="Listen">
            <switch href =http://wap.cnet.com/news.wml/>
        </do>
    </card>
</wml>
```

In this application the developer provides a listen button to the user if the user wants to listen to the content of http://wap.cnet.coM/news.wml.

The Multi-Mode platform translates the switch in the following way:

```
<wml>
    <card title="News Service">
        <p>
            Cnet news
        </p>
        <do type="options" label="Listen">
            <go
            href =http://Multi-
            ModePlatform_IP_Address:port/SwitchContextToVoice.jsp
            ? url=http://wap.cnet.com/news.wml"/>
        </do>
    </card>
</wml>
```

This will allow user to switch the context to voice by pressing the listen button.

One method of switching to voice mode from visual mode involves invoking a JSP/Servlet such as SwitchContextToVoice.jsp to do the switching. The following can be used to switch the context from visual to voice.
1. User presses the listen button.
2. The action to listen button is the SwitchContextToVoice.jsp which does the switch context.
3. The SwitchContextToVoice.jsp initiates a client request to switching server 860 in order to switch the context from visual to voice 4. The user passes the WML link say http://www.abc.com/xyz.wml that user wants to listen to the switching server 860.
5. The switching server 860 uses the state server 815 to save the URL link user wants to listen to as the state of the user.
6. The switching server 860 then uses the wtai protocol to initiate a normal voice call and disconnects the current WAP session.
7. The user gets connected with the VoiceXML compliant browser (HeyAnita, BeVocal, Telera etc).
8. The VoiceXML browser calls a JSP/Servlet say Startvxml.jsp that checks what kind of content user wants to listen. The startvxml.jsp uses the state server to get the state of the user i.e. the URL link it wants to listen to.
9. Startvxml.jsp checks if the URL link that user want to listen is in appropriate format (VoiceXML) for the voice browser to play it. If the URL link is a valid VoiceVXML then the VoiceXML browser plays the content of the link. Else if the link is in form (e.g. WML, HDML, iMode etc.) not suitable for voice browser then the JSP/Servlet fetches the content of URL link and converts it into valid VoiceXML source. The VoiceXML browser then plays the converted VXML source. If the link is pointing to an audio format file then the VoiceXML browser plays that audio file. If the text attribute is present then the inline text is encapsulated within a valid VoiceXML file and then the VoiceXML browser plays the inline text.

listen

<listen text="" "url=" VOICE_URL "next=" WML_URL">

| Attribute | Description |
| --- | --- |
| Text | text is the inline text message the developer want to listen |
| url | url is the link the developer wants to listen. |
| Next | Optional - next is the URL where the control flow begin once the 'url' attribute is played. If not present the flow is sequential. |

Note:
Either url attribute or text attribute is present. One of them should always be present in the exemplary embodiment described herein.

The LISTEN tag is intended for use with 2.5/3.0G phones, which allows initiating a voice session while a data session remains active. The LISTEN leverages the simultaneous dual channel capability of 2.5/3.0G phones. When the LISTEN tag is executed, the current data session remains active and a voice session is initiated, which executes the VOICE_URL specified in the 'url' attribute of the LISTEN tag.

The URL could be in any form. If the URL is not in appropriate voice form, here VoiceXML, then it is converted by the multi-mode platform into appropriate voice form as described.

The multi-mode platform 812 provides the necessary synchronization and state management needed to coordinate between the voice and data channel active at the same time.

Figure 9:
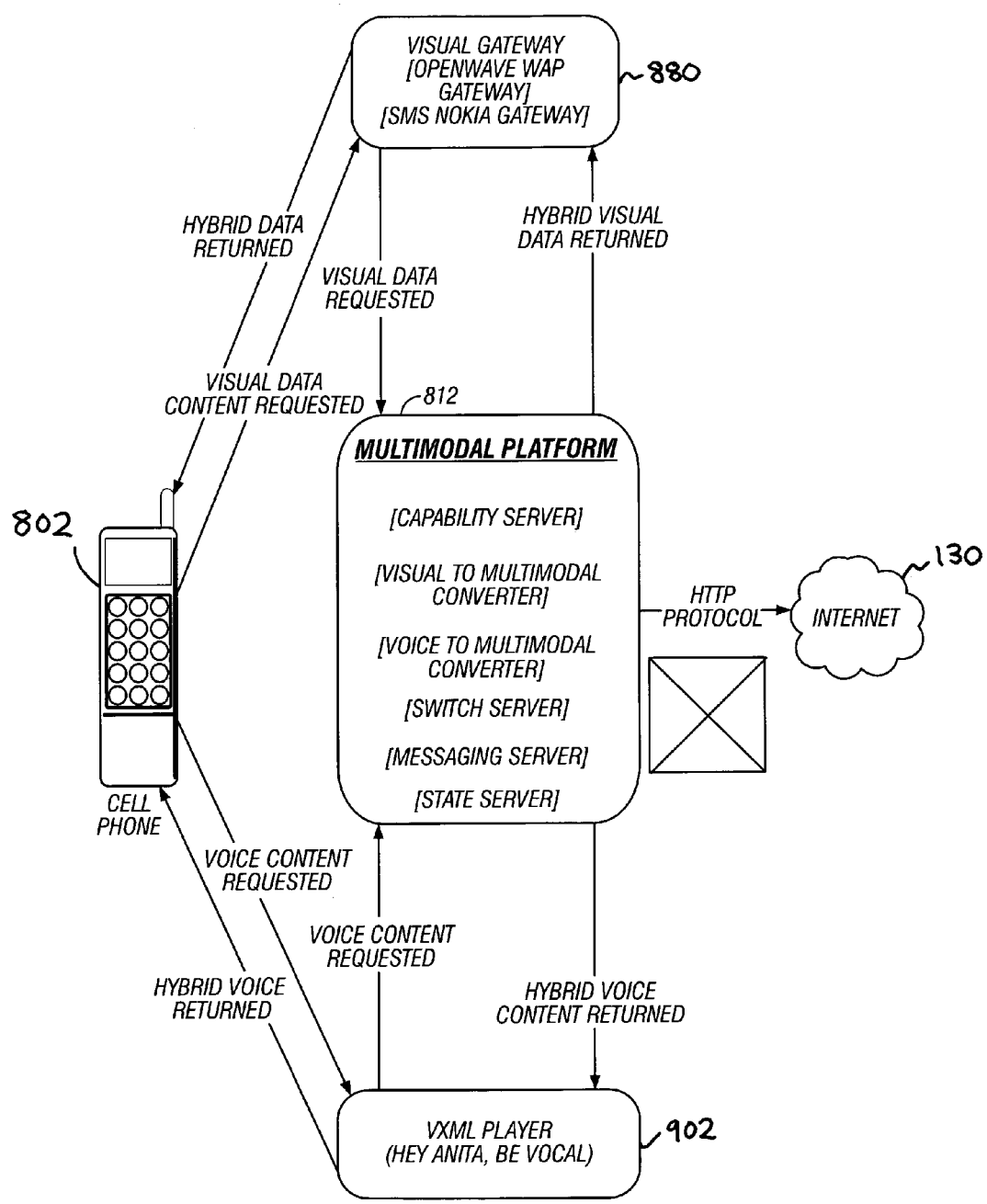
FIG. 9 illustratively represents an exemplary system environment within which a multi-mode platform of the present invention may be deployed.

As mentioned above, the multi-mode platform (FIG. 9) processes the Multi-modal tags by translating them into corresponding valid visual/voice markup language. The multi-mode platform allows the user to write multi-modal application information by using the Multi-modal tags. Also any content that does not use the Multi-modal tags is automatically converted into multi-modal content when accessed through multi-mode platform. The user has the option of turning off the automatic conversion process by directing the multi-mode platform using the meta tags.

Automatic conversion of visual/voice content into Multimodal Content

In voice-based markup languages such as VoiceXML, any VoiceXML source that is accessed through multi-mode platform is automatically converted into multi-modal content by putting show grammar at appropriate place. The presence of show grammar allows the user to say show at any time and the multi-mode platform switches the context from active voice based VXML to corresponding visual content.

```
<vxml>
    <link caching ="safe"
    next ="<http://Multi-
    ModePlatform_IPAddress:port/SwitchContextToVoice.jsp?
    phoneNo=session.telephone.ani&url=currentUrl&
    title=NetAlert"/>
        <grammar>
                [ show ]
            </grammar>
    </link>
    <form id="formid">
    </form>
</vxml>
```

The user can disable the automatic conversion of voice-based content (VoiceXML) into multi-modal by following way:

<vxml multi-modal="false"> this will direct the multi-mode platform that this content should not be converted into multi-modal. The default value of multi-modal is always true.

Also, the automatic multi-modal and the <switch> are generally exclusive. That is, if the <switch> tag is already used in the VXML source, then the multi-mode platform will not do the automatic multi-modal conversion.

In a visual based markup language such as WML, any WML source that is accessed through the multi-mode platform is automatically converted into multi-modal content by putting a listen button at the appropriate place. The presence of listen button allows the user to press listen button at any time and the multi-mode platform switches the context from visual session to voice session. The current visual content is converted in accordance with the voice-based content such as VoiceXML using the conversion server 150. The converted content is then executed by a VoiceXML compliant platform (HeyAnita, TelEra, BeVocal etc.).

The following is a simple WML application lacking a listen button.

```
<wml>
    <head>
        <meta http-equiv="Cache-Control" content="must-revalidate"/>
        <meta http-equiv="Expires" content="Tue, 01 Jan 1980 1:00:00 GMT"/>
        <meta http-equiv="Cache-Control" content="max-age=0"/>
    </head>
    <card title="Hello world">
        <p mode="wrap">
            Hello world!!
        </p>
    </card>
</wml>
```

When above application is accessed through multi-mode platform, the platform automatically makes it Multi-Mode WML.

The following is the converted multi-modal content with a listen tag in it:

```
<wml>
    <head>
        <meta http-equiv="Cache-Control" content="must-revalidate"/>
        <meta http-equiv="Expires" content="Tue, 01 Jan 1980 1:00:00 GMT"/>
        <meta http-equiv="Cache-Control" content="max-age=0"/>
    </head>
    <template>
        <do type="options" label="Listen">
            <go href="http://Multi-ModePlatform_IP_address:port/SwitchContextTo
            Voice.jsp?url=currentWML/>
            </do>
    </template>
    <card title="Hello world">
        <p mode="wrap">
            Hello world!!
        </p>
    </card>
</wml>
```

The above application displays "Hello World" on the screen of the subscriber unit 802. The user of the subscriber unit 802 can press listen at any time and the user can listen to the spoken "Hello World". The SwitchContextToVoice.jsp uses the conversion server 850 to convert the current visual content (e.g., WML) into voice content (VoiceXML) and switches the context to voice mode.

The user can disable the automatic conversion of visual-based content (e.g., WML) into multi-modal by following way:

<wml multi-modal="false"> this will direct the multi-mode platform that this content should not be converted into multi-modal. The default value of multi-modal is always TRUE.

Also, the automatic multi-modal and the <switch> are generally exclusive. That is, if the <switch> tag is already used in the WML source, then the multi-mode platform will not carry out the automatic multi-modal conversion.

The messaging server 824 is responsible for sending visual content in appropriate form to the user. The switching server requests the messaging server in order to send visual content to the user and then disconnects the current voice session. The successful delivery of visual content by the messaging server confirms the context switch from voice to visual. The switching server 860 uses the capability server 870 in order to find out if the user is capable of receiving SMS or WML content.

If the user is capable of receiving WML content, then push server 874a is used to push the content to the user. The push server uses the standard WAP gateway in order to push the WML content to the phone.

Else if the user is capable of receiving SMS, then SMS server 874b is used to send SMS messages to the user. The SMS server uses the standard SMS gateway in order to send SMS message to the phone.

The SMS server 874b is also used when <show> tag is used in the voice markup language (VoiceXML). When the SMS server is initiated, because of the <show> tag, the SMS server also provides the necessary synchronization between the two concurrent sessions: voice and visual. In this case when <show> tag is used, the SMS server delivers the SMS message and when the SMS is successfully delivered to the phone, the SMS server starts playing the voice source specified in the next attribute of the <show> tag.

Intelligent Switching Mechanism for Multi-Mode Information Retrieval System

The conversion server 850, when used with the multi-mode platform 812 (also identified herein as the MultiMode Gateway Controller or MMGC 812) is capable of providing multimodal content to the user. As discussed above, existing visual content is converted into voice form by the conversion server 850, and the MMGC 812 adds visual interfaces in the created voice content to allow the user to switch back to visual content while voice browsing the content. In addition, once a user starts voice browsing the content and wishes to be switched back to visual mode, the user is taken back to visual mode, but may also view the content previously browsed in voice mode. The following sections describe a method enabling a user to switch back and forth between visual and voice modes when browsing different subsection of a given page of content.

In following discussion WML is used as visual markup language for example. However the technique is independent of any visual markup language and can be applied on any of the other wireless markup languages such as WML, xHTML, cHTML etc.

The scripts used in the examples are defined in a generic way but can be any of the scripting used by the developer such as PHP, JSP, ASP, PERL, SERVLETS, JAVA etc.

The following section describes the different type of switching state management supported by the MMGC 812. The examples are provided to understand the switching process.

Page-Based & Link-Based Switching Methods

By way of background, a few examples are provided to illustrate the operation of the MMGC 812 in supporting various page-based and link-based switching methods. In order to aid understanding, in the following examples, the visual content is described as being provided in both xHTML and WML.

Page-Based Switching

During operation in this mode, the state of the user is saved on a page-by-page basis. (see, e.g., Example 1 below). That is, page-based switching granularity is supported. This means that if a user is browsing a page in visual mode and mode is switched to voice, the user will listen to the same page that the user was browsing in visual mode. The same holds true when switching from voice to visual.

EXAMPLE 1

The following is a simple WML application without listen capability.

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <head>
        <meta http-equiv="Cache-Control" content="must-revalidate"/>
        <meta http-equiv="Expires" content="Tue, 01 Jan 1980 1:00:00 GMT"/>
```

```
        <meta http-equiv="Cache-Control" content="max-age=0"/>
    </head>
    <card title="Press">
        <p mode="nowrap">
            <do type="accept" label="OK">
                <go href="mail$(item:noesc).wml"/>
            </do>
            <big>Inbox</big>
            <select name="item">
                    <option value="1">
                        James Cooker Sub:Directions to my home
                    </option>
                    <option    value="2">John    Hatcher
                    Sub:Directions </option>
            </select>
        </p>
    </card>
</wml>
```

When the above source is accessed through the MMGC 812, it operates to automatically generate multi-mode content.

The following is the converted multi-modal content with a listen tag:

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <head>
        <meta http-equiv="Cache-Control" content="must-
revalidate"/>
        <meta http-equiv="Expires" content="Tue, 01 Jan 1980
1:00:00 GMT"/>
        <meta http-equiv="Cache-Control" content="max-age=0"/>
    </head>
    <template>
        <do type="options" label="Listen">
            <go
            href="http://MMGC_IPADDRESS/scripts/SwitchContext
            ToVoice.Script?url=currentWML/>
                    </do>
    </template>
    <card title="Press">
        <p mode="nowrap">
            <do type="accept" label="OK">
                <go
                href="http://MMGC_IPADDRESS/scripts/multimo
                de.script?url=mail$(item:noesc).wml"/>
            </do>
            <big>Inbox</big>
            <select name="item">
                    <option value="1">
                        James Cooker Sub:Directions to my home
                    </option>
                    <option    value="2">John    Hatcher
                    Sub:Directions </option>
            </select>
        </p>
    </card>
</wml>
```

The similar visual source in xHTML would look like as follows:

```
<?xml version="1.0"?>
    <!DOCTYPE html PUBLIC "-//WAPFORUM//DTD XHTML
    Mobile
    1.0//EN" "http://www.wapforum.org/DTD/xhtmlmobile10.dtd">
    <html xmlns="http://www.w3.org/1999/xhtml" >
```

```
        <head>
            <title>Email Inbox</title>
        </head>
        <body>
            <p>Inbox<br/>
            1. <a href="mail1.xhtml" >James Cooker Sub: Directions
to my home</a><br/>
            2. <a href="mail2.xhtml" > John Hatcher Sub:Directions
</a><br/>
            </p>
        </body>
</html>
```

This xHTML visual source is accessed via the MMGC 812, and converted into MultiMode xHTML by adding voice interfaces in the visual source. The resultant MultiMode xHTML looks as follows:

```
<?xml version="1.0"?>
<!DOCTYPE html PUBLIC "-//WAPFORUM//DTD XHTML Mobile
1.0//EN"
"http://www.wapforum.org/DTD/xhtmlmobile10.dtd">
<html xmlns="http://www.w3.org/1999/xhtml" >
    <head>
        <title>Email Inbox</title>
    </head>
    <body>
        <p>Inbox<br/>
        <a
href="http://MMGC_IPADDRESS/scripts/SwitchContextToVoice.
Script?u
rl=currentxHTML">Listen</a><br/>
            1. <a href="mail1.xhtml" >James Cooker Sub: Directions
to my home</a><br/>
            2. <a href="mail2.xhtml" > John Hatcher Sub:Directions
</a><br/>
            </p>
        </body>
</html>
```

In this example, the user can press LISTEN anywhere in the visual page, but the VoiceXML server will always take the user to top of the current visual page in voice mode. The addition of a <template> tag enables a user to browse the content in voice mode as well. The <template> tag here provides an additional option of LISTEN. The LISTEN soft key instructs the MMGC 812 to initiate the voice session, save the current state of the user and provides an environment in which user can browse the content using voice.

Link-Based Switching

During operation in the link-based switching mode, the SWITCH function is not applied on the whole page. Instead, a selective switch is done is performed in this case. When a user switches from visual to voice, the user can specify which page to browse when the mode is switched to voice. This is useful when a user wants to switch to voice mode on a menu item in a WML page and then voice browse the content of the link when the switch mode is performed.

EXAMPLE 2

```
<?xml version="1.0"?>
<!DOCTYPE   wml PUBLIC   "-//WAPFORUM//DTD   WML   1.1
```

-continued

```
//EN"
"http://www.wapforum.org/DTD/wml_1.1.xml">
<wml>
    <card title="Press">
        <p mode="nowrap">
            <do type="accept" label="OK">
                <go href="mail$(item:noesc).wml"/>
            </do>
            <do type="options" label="Listen">
                <switch url="mail$(item:noesc).wml"/>
            </do>
            <big>Inbox</big>
            <select name="item">
                <option value="1">
                    James Cooker Sub:Directions to my home
                </option>
                <option value="2">John Hatcher
                    Sub:Directions </option>
            </select>
        </p>
    </card>
</wml>
Similar xHTML would be as follows:
<?xml version="1.0"?>
<!DOCTYPE html PUBLIC "-//WAPFORUM//DTD XHTML Mobile
1.0//EN"
"http://www.wapforum.org/DTD/xhtmlmobile10.dtd">
<html xmlns="http://www.w3.org/1999/xhtml" >
    <head>
        <title>Email Inbox</title>
    </head>
    <body>
        <p>Inbox<br/>
        <a href="mail1.xhtml" >James Cooker Sub: Directions to
        my home</a><br/>
        <a
        href="http://MMGC_IPADDRESS/scripts/
        SwitchContextToVoice.
        Script?url=mail1.xhtml">Listen</a><br/>
        <a href="mail2.xhtml" > John Hatcher Sub:Directions
        </a><br/>
        <a
        href="http://MMGC_IPADDRESS/scripts/
        SwitchContextToVoice.
        Script?url=mail2.xhtml">Listen</a><br/>
        </p>
    </body>
</html>
```

In this example, when user presses LISTEN on any of the email options, the MMGC 812 disconnects the data call and starts a voice call to VoiceXML server. The VoiceXML server fetches mail*.wml (corresponding email) from the content server and executes it as a voice command. This operation is called link-based switching; where user presses LISTEN on a link and then listens to the content of the link.

Subsection-Based Switching

Subsection-based switching allows a content to be browsed partly in visual form and partly in voice form. The mode differs from the above-described page-based switching mode in that subsection-based switching permits a user to browse a page partly in voice and partly in data. In contrast, during page-based switching, an entire content page is browsed entirely in either a visual or audible fashion.

As mentioned above, subsection-based switching can be implemented either in an environment where visual content is automatically converted into voice form (VoiceXML) or can be implemented where a visual content uses an XML tag <switch> to switch to voice as needed by the application. In both cases, the mechanism to implement subsection based switching remains the same.

In order to switch to voice mode when subsection-based switching is available as a selectable option, the following is required by MMGC 812
1) The VoiceXML compliant server.
2) The URL to be browsed in voice once the mode is switched to voice from visual.
3) Whether subsection-based switching is to be applied or not.

The VoiceXML gateway 902 is provided either by the carrier or the enterprise using the MMGC 812. The URL is furnished by the application developer. The URLI could be in any of the visual based XML languages such as WML/cHTML/xHTML etc. or in voice based XML languages such as VoiceXML. The MMGC 812 identifies the type of the URL and then applies appropriate conversion rules to make the content suitable to be browsed using voice. The converter is used to convert the visual source into MultiModal VoiceXML, which provides the ability to come back to visuals depending on the user's choice.

Techniques for Subsection Based Switching

As mentioned above, the conversion of existing content into multi-modal content is performed in accordance with a set of conversion rules. In order to accommodate subsection switching, these rules are extended as described herein. Whether or not subsection-based switching will be available with respect to various items of existing content will generally be a configurable parameter. If subsection-based switching is to be available, the following rules are applied during the process of converting the existing visual-based source content into MultiMode VoiceXML.

The MultiMode subsection-based switching algorithm divides the visual source into multiple parts. Start and end of the part is based on delimiter rules defined by MMGC 812. The subsection-based switching is particularly useful when a visual text is presented to the user for reading usually in the form of a paragraph using XML tag <p>. In most of the common visual-based languages such as xHTML and WML, the text is presented using the XML tag <p>. Let it be assumed that <p> is the XML tag used in most of the visual markup languages. Other languages may use other nomenclature for this "<p> tag", but the concepts remain the same.

Figure 11A:
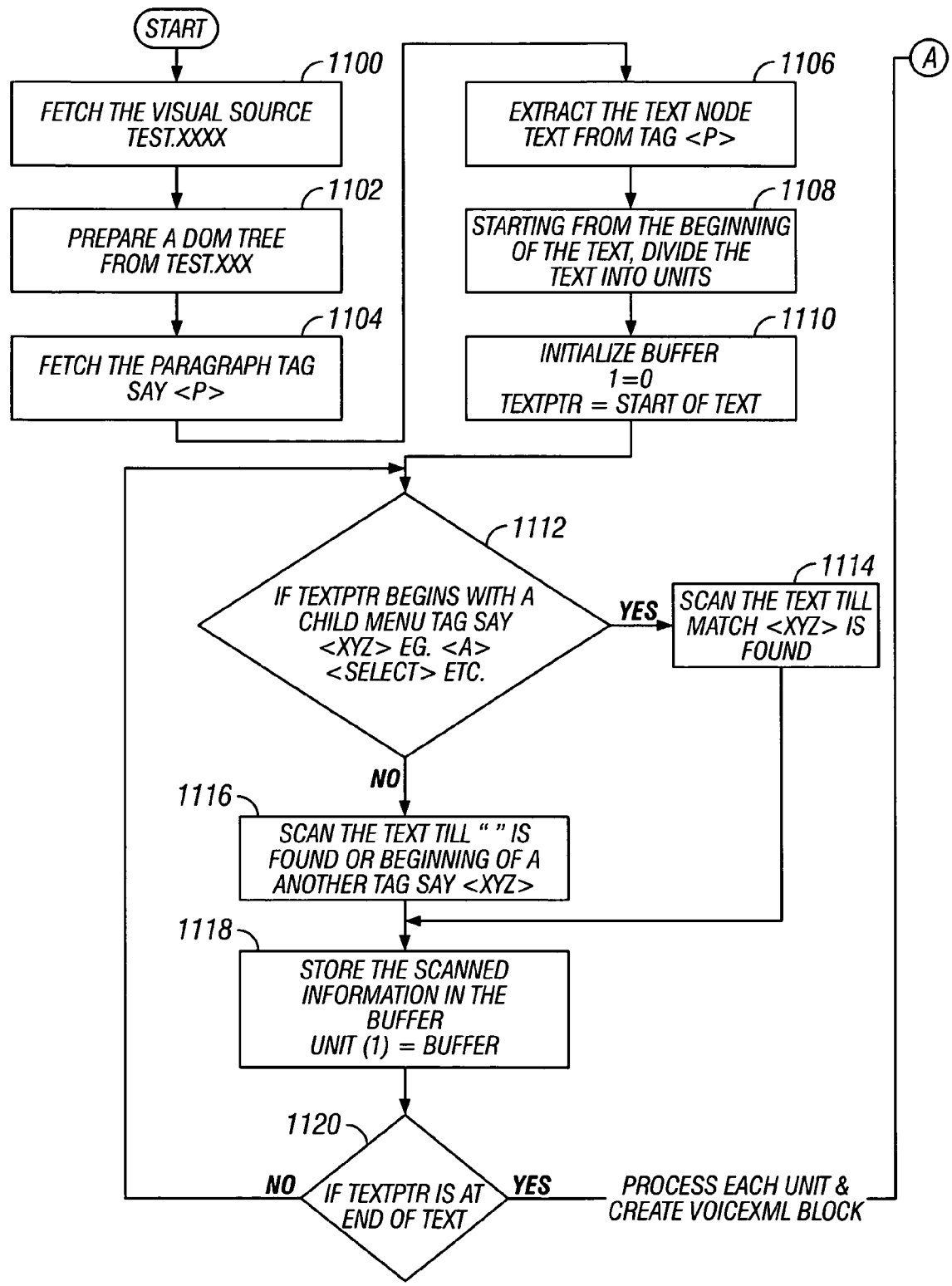
FIG. 11 is a flow chart which illustratively represents an exemplary process for subsection-based switching in accordance with the present invention.
Figure 11B:
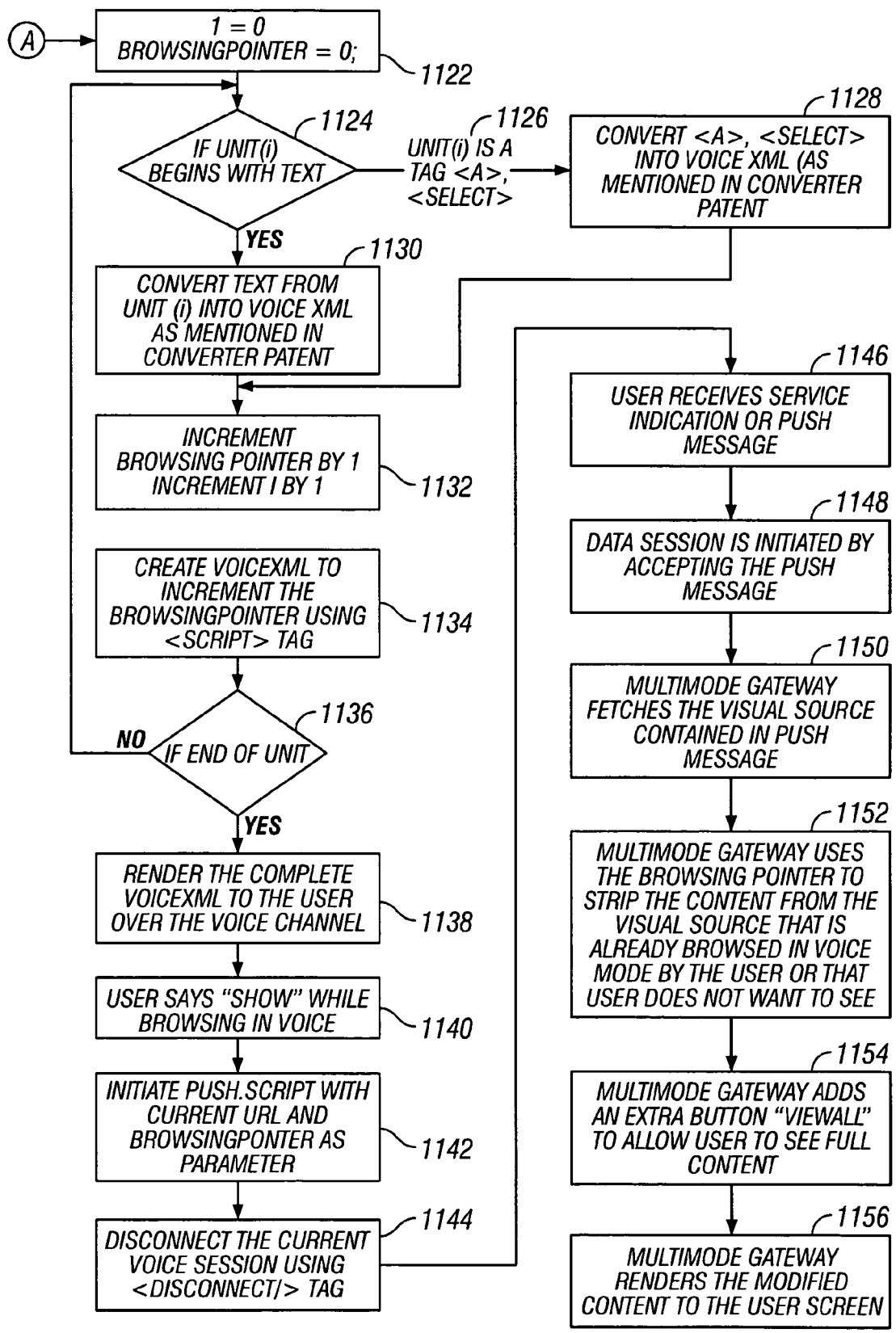

FIG. 11 is a flow chart which represents an exemplary process for subsection-based switching:

FIG. 11 shows the visual source is first obtained at 1100. As described previously, a DOM and the tree is prepared from the visual source at 1102. The tag which represents delineation of paragraphs, here that <p>tag is fetched at 1104. This has the effect of delineating the text within the key tag according to the delineating rules. The text is extracted at 1106, and divided into units at 1108.

A unit is a text delimited either by a period '.' Or by '\n' or by start of another tag such as<select>, <a>, <anchor>, <submit>, <input> etc. The tags that formats the text are ignored and are not used as the delimiters such as <b>, <big>, <small>. These format tags are only ignored for subsection based processing i.e. these are not used as a mark.

The <p> can have tags inside as per WML or xHTML standard or any other visual markup standard.

If a tag such as <select> or <a> is found inside the <p> tag the whole tag (start and end of the tag) in this case <select> xyz </select> or <a href="URL"> title</a> forms a separate unit. That is start of a tag inside <p> tag is beginning of a new unit and the corresponding end tag ends the current unit.

1110 begins a process of converting each unit individually, allowing each unit to be individually converted. 1112 determines if a child menu tag is shown, and if so the text represented by that child menu tag is scanned at 1114. If not, the text itself is scanned at 1116 until another tag is found. The scanned information is stored in the buffer at 1118. This process continues at 1120 until the text block is ended.

Since the operation keeps track of these different sub modes, it facilitates keeping track of each unit even when browsing in VoiceXML. At the end of the text 1122, 1124*b* determines if the next unit begins with text. If not, it is determined it to be a tag at 1126 and converted into a VoiceXML tag at 1128. If the unit is text, and the text is converted at 1130 into VoiceXML. The counters are incremented at 1132 and 1134 and at end of unit is detected at 1136.

The complete VoiceXML document is then provided to the user at 1138. This allows different operations. For example as in above, the user can say the word SHOW during the voice browsing to provide textual content. This enables a push script at 1142 and disconnects the voice session at 1144. The message is received at 1146 and the data session initiated at 1148. The multi-modal gateway fetches the visual source at 1150 and uses the browsing pointer to strip the content from the visual source at 1152. It also adds an additional Multi-modal tag for user all at 1154 and provides information to the screen at 1156. In this way, the MMGC 812 keeps updating the browsing pointer as the user browses each unit and moves to next unit in a voice session.

When user says SHOW to go back to visuals, the current browsing position is used by MMGC 812 to take the user to same place where the user was in voice. The MMGC 812 takes following actions:

Fetches the visual source to be loaded.

Uses the voice browsing pointer to strip the content that is already being browsed in voice. The stripping is done intelligently so new visual source is syntactically correct. (Explained later)

MMGC 812 adds an extra option in the modified visual source to view the full page. This allows the user to see the full content not the modified one.

The modified content is now rendered to the mobile device using the wireless gateway.

EXAMPLE 3

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <card title="Press">
        <p mode="nowrap">
            <do type="accept" label="OK">
                <go href="mail$(item:noesc).wml"/>
            </do>
            <do type="options" label="Listen">
                <switch url="mail$(item:noesc).wml"/>
            </do>
            <big>Inbox</big>
            <select name="item">
                <option value="1">
                    James Cooker Sub:Directions to my
                    home
                </option>
                <option value="2">John Hatcher
                    Sub:Directions </option>
            </select>
        </p>
    </card>
</wml>
Similar xHTML
```

-continued

```
<?xml version="1.0"?>
<!DOCTYPE html PUBLIC "-//WAPFORUM//DTD XHTML Mobile
1.0//EN" "http://www.wapforum.org/DTD/xhtmlmobile10.dtd">
<html xmlns="http://www.w3.org/1999/xhtml".>
    <head>
        <title>Email Inbox</title>
    </head>
    <body>
        <p>Inbox<br/>
        <a href="mail1.xhtml" >James Cooker Sub:
        Directions to my home</a><br/>
        <a
        href="http://MMGC_IPADDRESS/scripts/SwitchContext
        ToVoice.Script?url=mail1.xhtml">Listen</a><br/>
        <a href="mail2.xhtml" >John Hatcher
Sub:Directions </a><br/>
        <a
        href="http://MMGC_IPADDRESS/scripts/SwitchContext
        ToVoice.Script?url=mail2.xhtml">Listen</a><br/>
        </p>
    </body>
</html>
```

Assuming the user selects the first email from James Cooker and starts browsing it visually. The source of this email in the WML format is set forth below:

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <card title="Press">
        <do type="accept" label="Listen">
            <switch url="mail1.wml"/>
        </do>
        <do type="options" label="Inbox">
            <go href="inbox.wml"/>
        </do>
        <p>
            Hi, Here are the driving directions to my
house. <br/>
            Total distance for this trip is 29
miles.<br/>
            There are total 7 steps.<br/>
            Step 1. Start going towards the AIRPORT EXIT
(0.4 mile).<br/>
            Step2. Continue on East Boston
Expressway/Summer Tunnel (1.1 mile).<br/>
            Step 3. Merge onto I 93 South (1.1
mile)<br/>
            Step 4. Merge onto I 90 West. (22.7
mile)<br/>
            Step 5. Take Route 9 exit towards
Framingham/Marlborough (1.2 miles)<br/>
            Step 6. Continue on Boston Worcester
Turnpike (0.4 miles) <br/>
        </p>
    </card>
</wml>
Similar xHTML:
<?xml version="1.0"?>
<!DOCTYPE html PUBLIC "-//WAPFORUM//DTD XHTML Mobile
1.0//EN" "http://www.wapforum.org/DTD/xhtmlmobile10.dtd">
<html xmlns="http://www.w3.org/1999/xhtml" >
    <head>
        <title>Email </title>
    </head>
    <body>
        <p>Inbox<br/>
        <a
href="http://MMGC_IPADDRESS/scripts/SwitchContextToVoice.Script?
url=currentxHTML">Listen</a><br/>
        </p>
        <p>
            Hi, Here are the driving directions to my
```

```
            house.
            Total distance for this trip is 29 miles.
            There are total 7 steps.
            Step 1. Start going towards the AIRPORT EXIT
(0.4 mile).
            Step2. Continue on East Boston
Expressway/Summer Tunnel (1.1 mile).
            Step 3. Merge onto I 93 South (1.1 mile).
            Step 4. Merge onto I 90 West. (22.7 mile).
            Step 5. Take Route 9 exit towards
Framingham/Marlborough (1.2 miles).
            Step 6. Continue on Boston Worcester
        Turnpike (0.4 miles).
        </p>
    </body>
</html>
```

When user presses "listen", a call is initiated and the WML/xHTML source is converted into VoiceXML. The call connects to the VoiceXML gateway. The gateway executes the converted VoiceXML using the VoiceXML interpreter. The MMGC 812 converts the WML/xHTML into VoiceXML and divides the VoiceXML into parts. Each part is marked by the MMGC 812. While browsing in voice, these marks are used to monitor the position of the user in a browsing session. When the user wants to return to visual mode, the marks are used to take the user to exactly the same position in the browsing session occupied by the user prior to switching to visual mode.

Various rules concerning the placement of these marks are described below.

Converted VoiceXML with V-Enable marks/tags:

```
<?xml version="1.0"?>
<vxml version="2.0" xmlns="http://www.w3.org/2001/vxml">
<catch event="show">
<prompt>You will be switched to visual mode in a moment</prompt>
<goto
next="http://MMGC_IPADDRESS/scripts/sendpush.Script?title=
Alert&
phoneNo=xxxxxxxxxx&url=http://urladdressofthevisualpage&
browsingpointer=expr(browingpointer)"/>
</catch>
<form id="test">
    <var name="browsingpointer" value="0"/>
    <block>
        <prompt>
            Hi, Here are the driving directions to my house.
        </prompt>
        <script>
            browsingpointer++;
        </script>
        <prompt>
            Total distance for this trip is 29 miles.
        </prompt>
        <script>
            browsingpointer++;
        </script>
        <prompt>
            There are total 7 steps.
        </prompt>
        <script>
            browsingpointer++;
        </script>
        <prompt>
            Step 1. Start going towards the AIRPORT EXIT
(0.4 mile).
        </prompt>
        <script>
            browsingpointer++;
        </script>
        <prompt>
            Step 2. Continue on East Boston Expressway/Summer
Tunnel (1.1 mile).
        </prompt>
        <script>
            browsingpointer++;
        </script>
        <prompt>
            Step 3. Merge onto I 93 South (1.1 mile).
        </prompt>
        <script>
            browsingpointer++;
        </script>
        <prompt>
            Step 4. Merge onto I 90 West. (22.7 mile).
        </prompt>
        <script>
            browsingpointer++;
        </script>
        <prompt>
            Step 5. Take Route 9 exit towards
Framingham/Marlborough (1.2 miles).
        </prompt>
        <script>
            browsingpointer++;
        </script>
        <prompt>
            Step 6. Continue on Boston Worcester Turnpike
(0.4 miles).
        </prompt>
        <script>
            browsingpointer++;
        </script>
    </block>
</form>
</vxml>
```

As may be apparent from inspection of the above code, the browsing position is incremented after every unit. The user is allowed to say SHOW at any time. When the user says SHOW, the associated SHOW event is caught by the VoiceXML interpreter and switch of mode is initiated by calling a script residing on the MMGC 812. The browsing pointer is passed as a parameter to this script. The script uses the browsing pointer value to strip off the content that is already browsed by the user in voice mode and displays it on the screen of the applicable subscriber unit 802.

The MMGC 812 uses this technique to convert any existing content or to provide XML tags for customized switching.

Automatic Conversion of Existing Visual Information into Subsections

The MMGC 812 operates to convert existing visual information into subsections capable of being "played" one at a time. This allows the applications to switch back from voice to visual on a particular subsection in the page. Any existing content can be converted into MultiModal form, which allows content to be browsed in voice mode as well.

EXAMPLE 4

The following is an example content of a news article from http://go.sosd.com

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
```

-continued

```
<head>
    <meta http-equiv="Cache-Control" content="max-age=0"
/>
</head>
<card id="story" title=" Bush, Blair seek Iraq accord">
    <do type="options" label="Back"><prev/></do>
    <p>
        09/07 5:24 PM<br/> WASHINGTON -- President Bush
        and British Prime Minister Tony Blair sought on
        Saturday to convince allies wary of military action
        that Iraq's Saddam Hussein is developing weapons of
        mass destruction and must be forcefully confronted.
        <br/> "This is a problem and we can't ignore
        it,"Blair said en route from London for a Camp
        David strategy session with Bush. <br/> The meeting
        came five days before Bush addresses the United
        Nations, where he is expected to challenge the
        international community to take quick, tough action to
        disarm Saddam or the United States will be obligated
        to act on its own to remove Saddam, according to
        advisers involved in writing the speech.
    </p>
</card>
</wml>
Similar xHTML:
<?xml version="1.0"?>
<!DOCTYPE html PUBLIC "-//WAPFORUM//DTD XHTML
Mobile 1.0//EN"
"http://www.wapforum.org/DTD/xhtmlmobile10.dtd">
<html xmlns="http://www.w3.org/1999/xhtml" >
    <head>
        <title>Bush, Blair seek Iraq accord</title>
    </head>
    <body>
        <p>
            09/07 5:24 PM<br/> WASHINGTON -- President Bush
            and British Prime Minister Tony Blair sought on
            Saturday to convince allies wary of military action
            that Iraq's Saddam Hussein is developing weapons of
            mass destruction and must be forcefully confronted.
            <br/> "This is a problem and we can't ignore
            it,"Blair said en route from London for a Camp
            David strategy session with Bush. <br/> The meeting
            came five days before Bush addresses the United
            Nations, where he is expected to challenge the
            international community to take quick, tough action to
            disarm Saddam or the United States will be obligated
            to act on its own to remove Saddam, according to
            advisers involved in writing the speech.
        </p>
    </body>
</html>
```

When above content is accessed through MMGC 812, it automatically transforms the content into MultiMode WML/xHTML with subsection switching enabled.

The following shows the converted multi-modal content with the listen tag and subsection switching enabled:

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <head>
        <meta http-equiv="Cache-Control" content="max-age=0"
/>
    </head>
    <template>
        <do type="options" label="Listen">
            <go
                href=http://MMGC_IPADDRESS/scripts/SwitchContextT
                oVoice.Script?url=currentWML&nested="true"/>
            </do>
    </template>
```

```
    <card id="story" title=" Bush, Blair seek Iraq accord">
        <onevent type="onenterbackward"><prev/></onevent>
        <do type="options" label="Back"><prev/></do>
        <p>
            09/07 5:24 PM<br/> WASHINGTON -- President Bush
            and British Prime Minister Tony Blair sought on
            Saturday to convince allies wary of military action
            that Iraq's Saddam Hussein is developing weapons of
            mass destruction and must be forcefully confronted.
            <br/> "This is a problem and we can't ignore
            it,"Blair said en route from London for a Camp
            David strategy session with Bush. <br/> The meeting
            came five days before Bush addresses the United
            Nations, where he is expected to challenge the
            international community to take quick, tough action to
            disarm Saddam or the United States will be obligated
            to act on its own to remove Saddam, according to
            advisers involved in writing the speech.
        </p>
    </card>
</wml>
Similar MultiMode xHTML:
<?xml version="1.0"?>
<!DOCTYPE html PUBLIC "-//WAPFORUM//DTD XHTML
Mobile 1.0//EN"
"http://www.wapforum.org/DTD/xhtmlmobile10.dtd">
<html xmlns="http://www.w3.org/1999/xhtml" >
    <head>
        <title>Bush, Blair seek Iraq accord</title>
    </head>
    <body>
        <p>
            <a
            href=http://MMGC_IPADDRESS/scripts/SwitchContextToVoic
            e.Script?url=currentxHTML&nested="true">Listen</a>
            09/07 5:24 PM<br/> WASHINGTON -- President Bush
            and British Prime Minister Tony Blair sought on
            Saturday to convince allies wary of military action
            that Iraq's Saddam Hussein is developing weapons of
            mass destruction and must be forcefully confronted.
            <br/> "This is a problem and we can't ignore
            it,"Blair said en route from London for a Camp
            David strategy session with Bush. <br/> The meeting
            came five days before Bush addresses the United
            Nations, where he is expected to challenge the
            international community to take quick, tough action to
            disarm Saddam or the United States will be obligated
            to act on its own to remove Saddam, according to
            advisers involved in writing the speech.
        </p>
    </body>
</html>
```

The addition of a listen button enables a user to browse the content in voice mode as well. The LISTEN soft key instructs the MMGC 812 to initiate the voice session with NESTED attribute set as TRUE and provide an environment in which the user can browse the content using voice.

The NESTED attribute tag instructs MMGC 812 to put marks in the content of the current page browsed by the user in visual mode. Once the MMGC 812 switches the user to voice mode, these marks are used to track the browsing position of the user in voice. And when user goes back to visual mode these marks are used to take the user to same position where the user was in voice mode.

XML Tag for Switching From Visual to Voice with Subsection

One potential disadvantage of automatic conversion of existing content is that it might not afford the user the opportunity to switch to a content page different from the page currently being browsed. In this regard, the above-described <switch> operation permits a user to switch to a particular page. The <switch> tag may be modified in order to allow a user to switch to a particular page, browse partially in voice mode, and then return in visual mode and browse the remainder of the page. Adding an attribute nested allows a user to specify whether or not switching as a function of subsections is to be enabled.

Syntax for modified <switch>:
<switch url="url_name" nested="true"/>

EXAMPLE 5

In this example, the following visual WML source is assumed to be generated for the Inbox of an account. The Inbox has two messages, and the user is permitted to switch between them. In addition, the NESTED attribute employed in the <switch> tag enables the switching mode to be changed from visual to voice.

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <card title="Press">
        <p mode="nowrap">
            <do type="accept" label="OK">
                <go href="mail$(item:noesc).wml"/>
            </do>
            <do type="options" label="Listen">
                <switch url="mail$(item:noesc).wml"
nested="true"/>
            </do>
            <big>Inbox</big>
            <select name="item">
                <option value="1">
                James Cooker Sub:Directions to my home
                </option>
                <option value="2">
                John Hatcher Sub:Meeting today 11.00
AM
                </option>
            </select>
        </p>
    </card>
</wml>
Similar xHTML:
<?xml version="1.0"?>
<!DOCTYPE html PUBLIC "-//WAPFORUM//DTD XHTML
Mobile 1.0//EN"
"http://www.wapforum.org/DTD/xhtmlmobile10.dtd">
<html xmlns="http://www.w3.org/1999/xhtml" >
    <head>
        <title>Email Inbox</title>
    </head>
    <body>
        <p>Inbox<br/>
        <switch url=mail1.xHTML nested="true" title="Listen">
        <a href="
http://MMGC_IPADDRESS/scripts/multimode.script?url=
mail1.xhtml">
        James Cooker Sub: Directions to my home</a><br/>
        <switch url=mail2.xHTML nested="true" title="Listen">
        <a href="
http://MMGC_IPADDRESS/scripts/multimode.script?url=
mail2.xhtml"> John Hatcher Sub:Directions </a><br/>
        </p>
    </body>
</html>
```

The NESTED attribute in the above <switch> tag instructs the MMGC 812 to put marks in the content of the URL specified in the "url" attribute above. Once the MMGC 812 switches the user to voice mode, these marks are used to track the browsing position of the user in voice. When the user returns to visual mode, these marks are used to take the user to same position occupied by the user during the browsing in voice mode.

EXAMPLE 6

The following example describes the conversion of more complex visual-based source content into multi-modal form. In this example, the <p> tag in WML source includes various child tags.

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <head>
        <meta http-equiv="Cache-Control" content="must-revalidate"/>
        <meta http-equiv="Expires" content="Tue, 01 Jan 1980
1:00:00 GMT"/>
        <meta http-equiv="Cache-Control" content="max-age=0"/>
    </head>
    <card title="MultiMode">
        <p mode="nowrap">
            Following applications will demonstrate the power of
            V-Enable's MMGC. Select any of the following
            application and experience the difference. <br/>
            <b>Multimode Applications: </b><br/>
            <a href="http://wap.cnet.com">Cnet News</a>
            <a href="http://www.bbc.co.uk/mobile/">BBC News</a>
            <a href="http://wap.yahoo.com">Yahoo Email</a>
            <a
href="http://MMGC_IPADDRESS/appl/email.Script">MultiMode
Email</a>
        </p>
    </card>
</wml>
```

Figure 12:
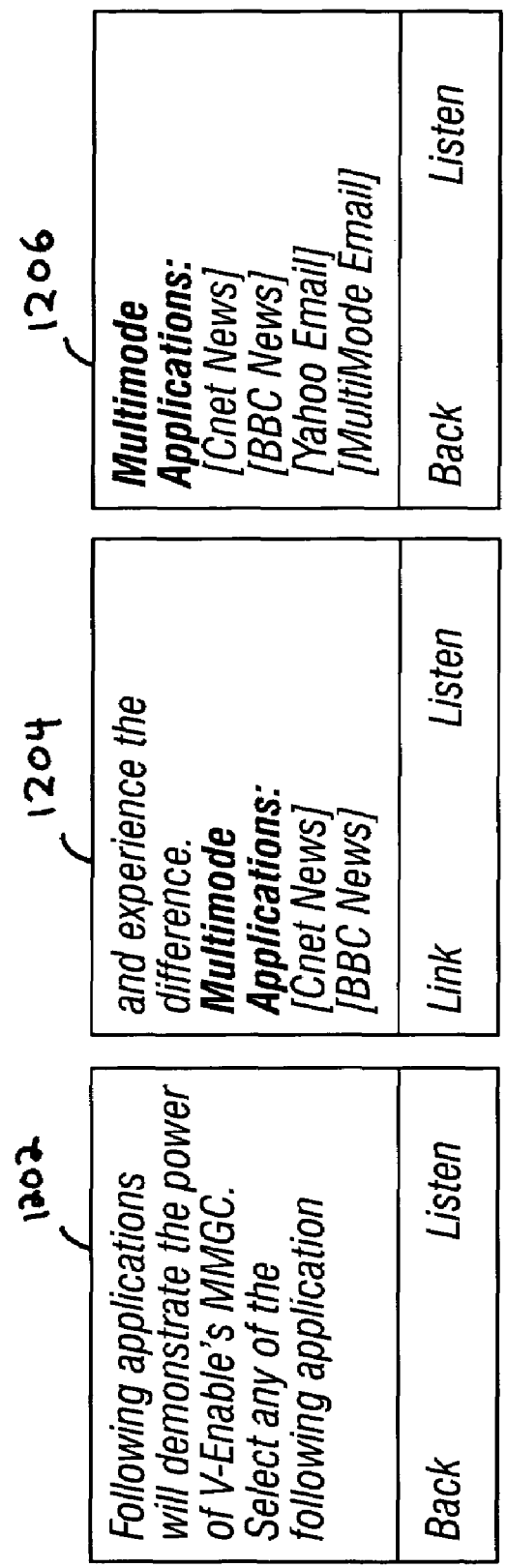
FIGS. 12–14 illustratively represents the manner in which certain source content would be visually rendered by a browser operative within a subscriber unit deployed within the system of FIG. 8.

FIG. 12 illustratively represents the manner in which the above source content would be rendered by a browser operative within the subscriber unit 802 (see boxes 1202, 1204, 1204). When the user selects LISTEN, visual source is accessed in voice through MMGC 812. The source is then converted by the MMGC 812 into MultiMode VoiceXML form, which includes a number of tags/marks:

```
<?xml version="1.0"?>
<vxml version="2.0" xmlns="http://www.w3.org/2001/vxml">
<catch event="show">
<prompt>You will be switched to visual mode in a
moment</prompt>
<goto
next="http://MMGC_IPADDRESS/scripts/sendpush.Script?title=Alert
&phoneNo=xxxxxxxxxx&url=http://urladdressofthevisual
page&browsingpointer=expr (browingpointer)"/>
</catch>
<var name="browsingpointer" value="0"/>
<form id="test">
    <block>
        <prompt>
            Following applications will demonstrate the
            power of V-Enable's MMGC.
        </prompt>
        <script>
            browsingpointer++;
        </script>
        <prompt>
            Select any of the following application and
            experience the difference.
        </prompt>
        <script>
            browsingpointer++;
        </script>
        <prompt>
            Multimode applications
        </prompt>
        <script>
```

```
                    browsingpointer++;
                </script>
            <block>
            <field name="noname">
                <prompt>cnet news</prompt>
                <prompt> Please Say Okay or next.</prompt>
                <grammar mode="voice" xml:lang="en-US"
version="1.0" root="command1">
                    <rule id="command1" scope="public">
                        <ruleref uri="#action1"/>
                    </rule>
                    <rule id="action1" >
                        <one-of>
                            <item>Okay</item>
                            <item>next</item>
                        </one-of>
                    </rule>
                </grammar>
                <filled>
                    <if cond="NONAME0 == 'okay'">
                        <goto
                        next="http://
http://MMGC_IPADDRESS/scripts/wml.Script?push
=1&phoneNo=xxxxxxxxxx&url=http://
wap.cnet.com"/>
                    <else/>
                        <prompt> next </prompt>
                    </if>
                </filled>
            </field>
            <script>
                browsingpointer++;
            </script>
            <field name="noname">
                <prompt>BBC news</prompt>
                <prompt> Please Say Okay or next.</prompt>
                <grammar mode="voice" xml:lang="en-US"
version="1.0" root="command1">
                    <rule id="command1" scope="public">
                        <ruleref uri="#action1"/>
                    </rule>
                    <rule id="action1" >
                        <one-of>
                            <item>Okay</item>
                            <item>next</item>
                        </one-of>
                    </rule>
                </grammar>
                <filled>
                    <if cond="NONAME0 == 'okay'">
                        <goto
                        next="http://
http://MMGC_IPADDRESS/scripts/wml.Script?push
=1&phoneNo=xxxxxxxxxx&url=http://
www.bbc.co.uk/mobile"/>
                    <else/>
                        <prompt> next </prompt>
                    </if>
                </filled>
            </field>
            <script>
                browsingpointer++;
            </script>
            <field name="noname">
                <prompt>Yahoo Email</prompt>
                <prompt> Please Say Okay or next.</prompt>
                <grammar mode="voice" xml:lang="en-US"
version="1.0" root="command1">
                    <rule id="command1" scope="public">
                        <ruleref uri="#action1"/>
                    </rule>
                    <rule id="action1" >
                        <one-of>
                            <item>Okay</item>
                            <item>next</item>
                        </one-of>
                    </rule>
                </grammar>
                <filled>
                    <if cond="NONAME0 == 'okay'">
                        <goto
                        next="http://
http://MMGC_IPADDRESS/scripts/wml.Script?push
=1&phoneNo=xxxxxxxxxx&url=http://
wap.yahoo.com"/>
                    <else/>
                        <prompt> next </prompt>
                    </if>
                </filled>
            </field>
            <script>
                browsingpointer++;
            </script>
            <field name="noname">
                <prompt>Multimode Email</prompt>
                <prompt> Please Say Okay or next.</prompt>
                <grammar mode="voice" xml:lang="en-US"
version="1.0" root="command1">
                    <rule id="command1" scope="public">
                        <ruleref uri="#action1"/>
                    </rule>
                    <rule id="action1" >
                        <one-of>
                            <item>Okay</item>
                        </one-of>
                    </rule>
                </grammar>
                <filled>
                    <if cond="NONAME0 == 'okay'">
                        <goto
                        next="http://
http://MMGC_IPADDRESS/scripts/wml.Script?push
=1&phoneNo=xxxxxxxxxx&url=http://
MMGC_IPADDRESS/appl/email.Script"/>
                </filled>
            </field>
        </form>
    </vxml>
```

As may be apparent from the above code, the browsing position is incremented after every unit in the generated VoiceXML. The user is also allowed to say "show" at any time. When the user says "show", the associated 'show' event is caught by the VoiceXML interpreter and switch of mode is initiated by calling a script residing on the MMGC 812. The browsing pointer is passed as a parameter to the script. The script uses the browsing pointer value to strip off the content that is already browsed by the user in voice mode and displays it on the mobile device screen. The difference between Example 3 and Example 6 is the presence of additional tags inside <p> tag.

Suppose the user while browsing in voice says "show" immediately after listening to "Following applications will demonstrate the power of V-Enable's MMGC". The MMGC 812 switches the user to visual mode and also pass the browsing pointer value as in Example 1. In this case the MMGC 812 removes the first unit since the value of the browsing pointer is one, and adds a soft key to view the whole page. The following visual source is then rendered to the mobile device:

```
<?xml version="1.0"?>
<!DOCTYPE wml PUBLIC "-//WAPFORUM//DTD WML
1.1//EN"
"http://www.wapforum.org/DTD/wml_1.1.xml">
<wml>
    <head>
        <meta http-equiv="Cache-Control" content="must-
revalidate"/>
```

-continued

```
        <meta http-equiv="Expires" content="Tue, 01 Jan 1980 1:00:00 GMT"/>
        <meta http-equiv="Cache-Control" content="max-age=0"/>
    </head>
    <template>
        <do type="options" label="ViewAll">
            <go href="urloforiginalcontent"/>
        </do>
    </template>
    <card title="MultiMode">
    <p mode="nowrap">
        Select any of the following application and experience the difference. <br/>
        <b>Multimode Applications: </b><br/>
        <a href="http://wap.cnet.com">Cnet News</a>
        <a href="http://www.bbc.co.uk/mobile/">BBC News</a>
        <a href="http://wap.yahoo.com">Yahoo Email</a>
        <a href="http://MMGC_IPADDRESS/appl/email.Script">MultiMode Email</a>
    </p>
    </card>
</wml>
```

Figure 13:
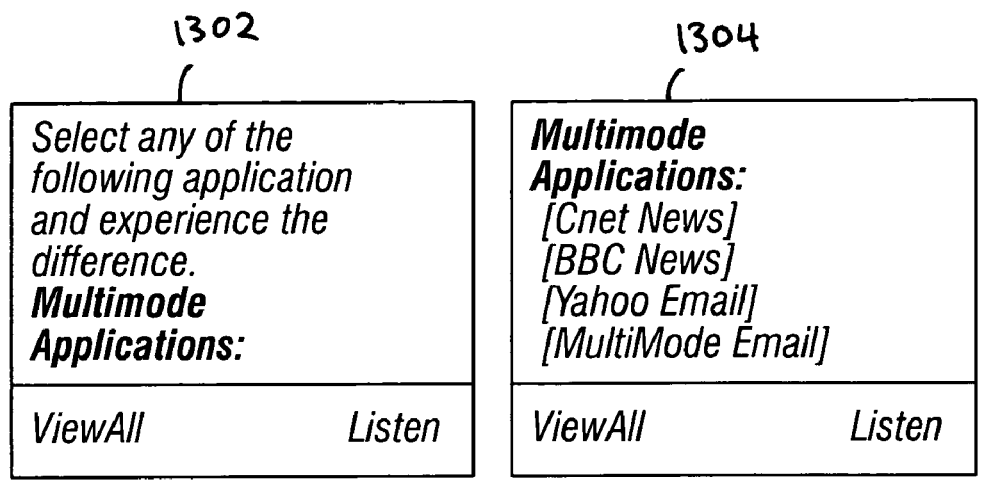

FIG. 13 depicts the visual source seen by the user in response to the above source (see boxes 1302, 1304). Note that the "ViewAll" softkey allows user to see the original content.

In another scenario, a user has listened to the text and has navigated up to BBC News and then says SHOW to switch to visual mode. The MMGC 812 switch the user to data mode and would pass the browsing pointer value as 4, which means that the user has already browsed four units of information. The MMGC 812 removes the first four units, since the browsing pointer is four. In addition, a soft key is added in order to view the whole page and render the following visual source to the mobile device:

```
<?xml version="1.0"?>
<!DOCTYPE wml PUBLIC "-//WAPFORUM//DTD WML 1.1//EN"
"http://www.wapforum.org/DTD/wml_1.1.xml">
<wml>
    <head>
        <meta http-equiv="Cache-Control" content="must-revalidate"/>
        <meta http-equiv="Expires" content="Tue, 01 Jan 1980 1:00:00 GMT"/>
        <meta http-equiv="Cache-Control" content="max-age=0"/>
    </head>
    <template>
        <do type="options" label="ViewAll">
            <go href="urloforiginalcontent"/>
        </do>
    </template>
    <card title="MultiMode">
    <p mode="nowrap">
        <a href="http://www.bbc.co.uk/mobile/">BBC News</a>
        <a href="http://wap.yahoo.com">Yahoo Email</a>
        <a href="http://MMGC_IPADDRESS/appl/email.Script">MultiMode Email</a>
    </p>
    </card>
</wml>
```

Figure 14:
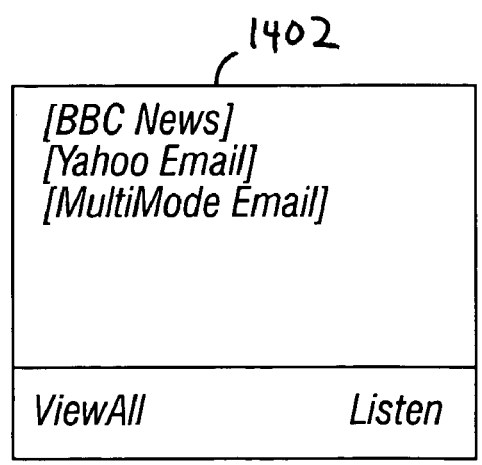

FIG. 14 shows the corresponding visual source seen by the user via the screen of the applicable subscriber unit 802 (see box 1402). Note that the "ViewAll" softkey allows user to see the original content.

Although only a few embodiments have been described in detail above, other modifications are possible.

What is claimed is:

1. A method, comprising:
receiving a document in a structured language which includes tags associated with portions of the document;
using said tags to provide a speech mark-up language version from said document; and
using said tags, and the same said document, to provide a visual mark-up language version from said document.

2. A method as in claim 1, further comprising playing speech corresponding to said speech mark-up language version.

3. A method as in claim 1, further comprising switching from one of said versions to the other of said versions.

4. A method as in claim 3, further comprising switching by determining a page that the user is currently using, and providing content and providing content for the same page in the other mark-up language.

5. A method as in claim 3, further comprising repeating currently viewed information during said switching.

6. A method as in claim 3, wherein said switching is carried out by initiating a special switching tag.

7. A method as in claim 3, wherein said switching out is carried out by initiating a link within the content.

8. A method as in claim 1, further comprising providing a document which can be used in both speech mark-up language mode and visual mark-up language mode at the same time.

9. A method as in claim 1, further comprising allowing the user to browse a document in said visual mark-up language, and accepting a command to provide additional content in said speech mark-up language version at the same time as providing said visual mark-up language version.

10. A method as in claim 1, further comprising allowing browsing a document in said speech mark-up language and accepting a command to provide additional content in said visual markup language at the same time.

11. A method as in claim 1, wherein said visual mark-up language is one which can be executed over a WAP browser.

12. A method as in claim 1, wherein said document is one which relates to e-mails.

13. A method as in claim 1, further comprising receiving a document with a SWITCH tag that allows a user to switch content from one of said mark-up versions to the other said mark-up versions.

14. A method as in claim 1, wherein said determining a need for visual mark-up language comprises determining if an initiating terminal has visual mark-up language capability.

15. A method as in claim 14, wherein said determining if the initiating terminal has visual mark-up capability comprises sending a message to the initiating terminal and determining if the initiating terminal completes registration based on the message.

16. A method as in claim 14, wherein the initiating terminal is a handheld telephone.

17. A method as in claim 14, wherein said determining if the initiating terminal has visual mark-up capability comprises informing the terminal to access a predetermined website which requires visual mark-up capabilities, and determining if the terminal has access to said website.

18. A method as in claim 17, further comprising using said determining to determine if the terminal has short message service capabilities.

19. A method as in claim 18, further comprising using said determining to determine if a message should be sent using SMS or SMTP.

20. A method as in claim 1, further comprising a SHOW tag which commands the terminal to show both voice mark-up mode and visual mark-up mode at the same time.

21. A method as in claim 20, wherein said show tag requests a server to send both voice mark-up information and visual mark-up information.

22. A method as in claim 1, wherein said visual mark-up language is one of WML, xHTML, or cHTML.

23. A method as in claim 1, further comprising allowing the content to be browsed partly in visual form and partly in voice form.

24. A method as in claim 23, further comprising dividing the source documents into multiple parts, and converting each of the multiple parts into either or both of visual mark-up language and/or voice mark-up language.

25. A system, comprising:
an information storage unit which stores a document in structured language that includes tags associated with portions of the document; and
a conversion server which allows converting said tags to provide both information in a voice mark-up language and information in a visual mark-up language, based on the same document.

26. A system as in claim 25, wherein said voice mark-up language is in VoiceXML.

27. A system as in claim 25, wherein said voice mark-up language is in a web compatible language.

28. A system as in claim 25, further comprising a portable terminal, which receives information from said conversion server, and displays said information from said conversion server.

29. A system as in claim 28, wherein said portable terminal is a handheld telephone.

30. A system as in claim 29, wherein said portable telephone keeps track of a currently browsed portion by unit numbers, and allows changing a currently browsed format.

31. A system as in claim 29, wherein said conversion server provides a duplicate version of the currently browsed portion responsive to said changing.

32. A system as in claim 25, wherein said conversion server is operative responsive to a command, to convert said information between voice mark-up language and visual mark-up language.

33. A system as in claim 32, wherein said information can be converted to either or both voice mark-up language and visual mark-up language.

34. A method a system as in claim 32, wherein said conversion server provides documents which have different units, each unit being separately marked as one or both of voice mark-up language and/or visual mark-up language.

35. A document containing data for use by a software application, the document comprising:
a structured format including text attributes and tag attributes, at least one of said text attributes being convertible into both a voice mark-up language and a visual mark-up language, and providing information which can be used in both said voice mark-up language and said visual mark-up language.

36. A document as in claim 35, wherein said voice mark-up language is VoiceXML.

37. A document as in claim 35, wherein said visual mark-up language is in a WAP compatible language.

38. A document as in claim 35, further comprising at least one tag enabling switching between format of contents.

39. A document as in claim 35, further comprising at least one tag enabling listening to contents during a visual browsing.

40. A document as in claim 35, further comprising at least one tag enabling showing of visual contents during a voice browsing session.

41. A document as in claim 35, further comprising tags which delineate different sections, wherein each section is separately delineated as being one or both of voice browsing or visual browsing.

42. A method, comprising:
providing first portion of a document on a portable phone in a voice mark-up language; and
providing a second portion of the same document on the portable phone, during the same browsing session, in a visual mark-up language.

43. A method as in claim 42, further comprising accepting a request from the portable phone to switch a mark-up language which is being displayed, and switching the mark-up language between visual mark-up language and speech mark-up language.

44. A method as in claim 42, further comprising accepting a request from the portable phone to display additional language, and displaying both speech mark-up language and visual mark-up language at the same time.

45. A method, comprising:
allowing a user to browse a document in either of voice XML or compact visual XML;
keeping track of the position of browsing in a current language; and
allowing switching from a current language to another language at a position related to said position of browsing.

* * * * *

UNITED STATES PATENT AND TRADEMARK OFFICE
CERTIFICATE OF CORRECTION

PATENT NO. : 7,054,818 B2
APPLICATION NO. : 10/761650
DATED : May 30, 2006
INVENTOR(S) : MULTI-MODAL INFORMATION DELIVERY SYSTEM

Page 1 of 1

It is certified that error appears in the above-identified patent and that said Letters Patent is hereby corrected as shown below:

On The Title Page
"Assignee: V-Enablo, Inc. " should be corrected to "Assignee: V-Enable, Inc."

Signed and Sealed this

Thirty-first Day of October, 2006

JON W. DUDAS
*Director of the United States Patent and Trademark Office*

(12) EX PARTE REEXAMINATION CERTIFICATE (7206th)
United States Patent
Sharma et al.

(10) Number: US 7,054,818 C1
(45) Certificate Issued: Dec. 1, 2009

(54) MULTI-MODAL INFORMATION RETRIEVAL SYSTEM

(75) Inventors: Dipanshu Sharma, San Diego, CA (US); Sunil Kumar, San Diego, CA (US); Chandra Kholia, San Diego, CA (US)

(73) Assignee: V-Enable, Inc., La Jolla, CA (US)

Reexamination Request:
No. 90/010,205, Jun. 23, 2008

Reexamination Certificate for:
Patent No.: 7,054,818
Issued: May 30, 2006
Appl. No.: 10/761,650
Filed: Jan. 14, 2004

Certificate of Correction issued Oct. 31, 2006.

Related U.S. Application Data
(60) Provisional application No. 60/439,981, filed on Jan. 14, 2003.

(51) Int. Cl.
*G10L 21/00* (2006.01)

(52) U.S. Cl. ............ 704/270; 704/270.1; 704/E15.045; 707/E17.006; 707/E17.119
(58) Field of Classification Search ................. None
See application file for complete search history.

(56) References Cited

U.S. PATENT DOCUMENTS

| 6,996,800 B2 | 2/2006 | Lucassen |
| 7,216,351 B1 | 5/2007 | Maes |

OTHER PUBLICATIONS

Nokia 3510 User's Guide, Nokia Corporation, © 2002.
Nokia 8890 User's Guide, Nokia Corporation, © 2000.
MyT–Mobile Internet Signup Web Page, T–Mobile USA, published at least as early as Oct. 17, 2002.
T–Mobile Internet Web Page, T–Mobile USA, published at least as early as Dec. 1, 2002.
T–Mobile E–Mail Web Page, T–Mobile USA, published at least as early as Oct. 22, 2002.

*Primary Examiner*—Woo H. Choi

(57) ABSTRACT

Multi-modal system which enables documents to be interpreted as either or both of voice browser-based documents and/or visual browser-based documents for a thin client such as a portable telephone. Special techniques and additions are added into the document to enable the document to be converted between voice markup and visual markup languages. In addition, the document can be simultaneously viewed in both of the voice markup and the visual markup languages. Special techniques are used to allow keeping track of the browsing position within this document.

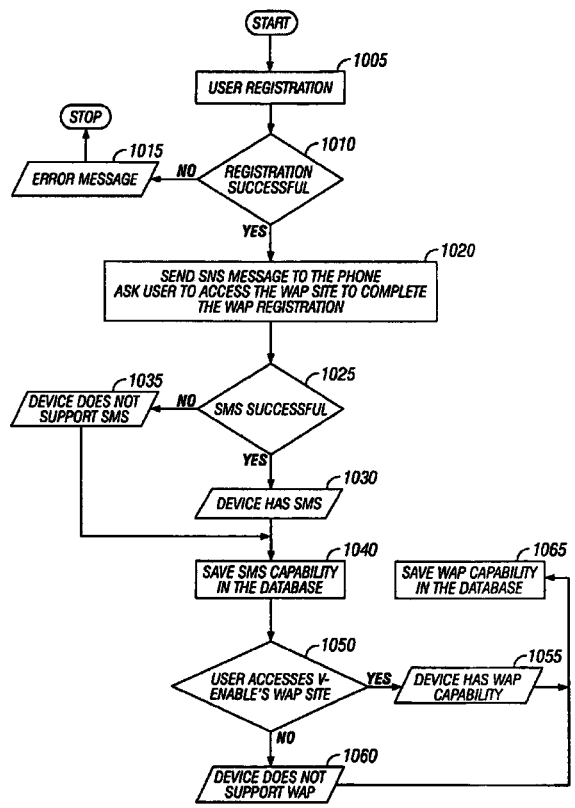

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 15 and 17–19 is confirmed.

Claims 1–14, 16 and 20–45 are cancelled.

* * * * *